US009696296B2

(12) United States Patent
Ramakrishnan et al.

(10) Patent No.: US 9,696,296 B2
(45) Date of Patent: Jul. 4, 2017

(54) TARGETING C-REL O-GLCNACYLATION AND USES THEREOF

(71) Applicant: California Institute of Technology, Pasadena, CA (US)

(72) Inventors: Parameswaran Ramakrishnan, Pasadena, CA (US); David Baltimore, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 471 days.

(21) Appl. No.: 14/166,681

(22) Filed: Jan. 28, 2014

(65) Prior Publication Data

US 2014/0212876 A1 Jul. 31, 2014

Related U.S. Application Data

(60) Provisional application No. 61/757,985, filed on Jan. 29, 2013.

(51) Int. Cl.
*A61K 31/00* (2006.01)
*G01N 33/50* (2006.01)
*A61K 31/513* (2006.01)
*A61K 31/655* (2006.01)
*A61K 31/7028* (2006.01)

(52) U.S. Cl.
CPC ....... *G01N 33/5023* (2013.01); *A61K 31/513* (2013.01); *A61K 31/655* (2013.01); *A61K 31/7028* (2013.01); *G01N 2440/38* (2013.01)

(58) Field of Classification Search
CPC .. G01N 3/5023; A61K 31/513; A61K 31/655; A61K 31/7028
See application file for complete search history.

(56) References Cited

U.S. PATENT DOCUMENTS

| 6,582,933 B1 * | 6/2003 | Okamoto | C07K 14/4702 435/252.3 |
| 2010/0055116 A1 * | 3/2010 | Liou | A61K 31/515 424/184.1 |

OTHER PUBLICATIONS

Allison et al., (PNAS. Oct. 16, 2012;109(42):16888-16893).*
Hwang et al., (BJ Pharmacol. Aug. 2013;169:1551-1560. Epub Jul. 12, 2013).*
Martin et al., (J Biochem. Aug. 11, 2000;275(32):24383-91).*
Xing et al., (PLoS ONE. Aug. 2011;6(8). e24021. pp. 1-10).*
Yang et al., (PNAS. Nov. 11, 2008;105(45):17345-17350).*
Golks et al., (EMBO J. Oct. 17, 2007;26(20):4368-79. Epub Sep. 20, 2007).*
Leeman et al., (Oncogene. Dec. 4, 2008; 27(3):6770-6781).*
Garbati et al., (Gene Expr. 2008;14(4):195-205).*
Baltimore, D. NF-kappaB is 25. Nat Immunol 12, 683-685 (2011).
Hayden, M.S. & Ghosh, S. NF-kappaB in immunobiology. Cell research 21, 223-244 (2011).

(Continued)

*Primary Examiner* — Cherie M Stanfield
(74) *Attorney, Agent, or Firm* — Knobbe Martens Olson & Bear LLP

(57) ABSTRACT

Serine 350 has been identified as the site of O-GlycNAcylation of c-Rel. Methods are provided for identifying compositions capable of blocking c-Rel activation. The methods generally involve identifying compounds that inhibit O-GlcNAcylation of c-Rel at the serine 350 residue, thereby preventing c-Rel activation and production of c-Rel-dependent cytokines.

18 Claims, 12 Drawing Sheets

(56) References Cited

OTHER PUBLICATIONS

Perkins, N.D. Post-translational modifications regulating the activity and function of the nuclear factor kappa B pathway. Oncogene 25, 6717-6730 (2006).
Leidner, J., Palkowitsch, L., Marienfeld, U., Fischer, D. & Marienfeld, R. Identification of lysine residues critical for the transcriptional activity and polyubiquitination of the NF-kappaB family member RelB. The Biochemical journal 416, 117-127 (2008).
Hart, G.W., Housley, M.P. & Slawson, C. Cycling of O-linked beta-N-acetylglucosamine on nucleocytoplasmic proteins. Nature 446, 1017-1022 (2007).
Hart, G.W., Slawson, C., Ramirez-Correa, G. & Lagerlof, O. Cross talk between O-GlcNAcylation and phosphorylation: roles in signaling, transcription, and chronic disease. Annual review of biochemistry 80, 825-858 (2011).
Zeidan, Q. & Hart, G.W. The intersections between O-GlcNAcylation and phosphorylation: implications for multiple signaling pathways. Journal of cell science 123, 13-22 (2010).
Slawson, C. et al. Perturbations in O-linked beta-N-acetylglucosamine protein modification cause severe defects in mitotic progression and cytokinesis. The Journal of biological chemistry 280, 32944-32956 (2005).
Zhang, S., Roche, K., Nasheuer, H.P. & Lowndes, N.F. Modification of histones by sugar beta-N-acetylglucosamine (GlcNAc) occurs on multiple residues, including histone H3 serine 10, and is cell cycle-regulated. The Journal of biological chemistry 286, 37483-37495 (2011).
Wang, Z. et al. Extensive crosstalk between O-GlcNAcylation and phosphorylation regulates cytokinesis. Science signaling 3, ra2 (2010).
Ozcan, S., Andrali, S.S. & Cantrell, J.E. Modulation of transcription factor function by O-GlcNAc modification. Biochimica et biophysica acta 1799, 353-364 (2010).
Chen, L.F., Mu, Y. & Greene, W.C. Acetylation of RelA at discrete sites regulates distinct nuclear functions of NF-kappaB. EMBO J 21, 6539-6548 (2002).
Zeidan, Q., Wang, Z., De Maio, A. & Hart, G.W. O-GlcNAc cycling enzymes associate with the translational machinery and modify core ribosomal proteins. Molecular biology of the cell 21, 1922-1936 (2010).
Yang, W.H. et al. Modification of p53 with O-linked N-acetylglucosamine regulates p53 activity and stability. Nat Cell Biol 8, 1074-1083 (2006).
Zachara, N.E. & Hart, G.W. O-GlcNAc modification: a nutritional sensor that modulates proteasome function. Trends in cell biology 14, 218-221 (2004).
Chatham, J.C. & Marchase, R.B. Protein O-GlcNAcylation: A critical regulator of the cellular response to stress. Current signal transduction therapy 5, 49-59 (2010).
Zachara, N.E., Molina, H., Wong, K.Y., Pandey, A. & Hart, G.W. The dynamic stress-induced "O-GlcNAc-ome" highlights functions for O-GlcNAc in regulating DNA damage/repair and other cellular pathways. Amino acids 40, 793-808 (2011).
Comer, F.I. & Hart, G.W. O-GlcNAc and the control of gene expression. Biochimica et biophysica acta 1473, 161-171 (1999).
Shafi, R. et al. The O-GlcNAc transferase gene resides on the X chromosome and is essential for embryonic stem cell viability and mouse ontogeny. Proc Natl Acad Sci U S A 97, 5735-5739 (2000).
O'Donnell, N., Zachara, N.E., Hart, G.W. & Marth, J.D. Ogt-dependent X-chromosome-linked protein glycosylation is a requisite modification in somatic cell function and embryo viability. Mol Cell Biol 24, 1680-1690 (2004).
James, L.R. et al. Flux through the hexosamine pathway is a determinant of nuclear factor kappaB-dependent promoter activation. Diabetes 51, 1146-1156 (2002).
Hattori, Y., Hattori, S., Sato, N. & Kasai, K. High-glucose-induced nuclear factor kappaB activation in vascular smooth muscle cells. Cardiovascular research 46, 188-197 (2000).
Yerneni, K.K., Bai, W., Khan, B.V., Medford, R.M. & Natarajan, R. Hyperglycemia-induced activation of nuclear transcription factor kappaB in vascular smooth muscle cells. Diabetes 48, 855-864 (1999).
Hofmann, M.A. et al. Insufficient glycemic control increases nuclear factor-kappa B binding activity in peripheral blood mononuclear cells isolated from patients with type 1 diabetes. Diabetes Care 21, 1310-1316 (1998).
Yuan, M. et al. Reversal of obesity- and diet-induced insulin resistance with salicylates or targeted disruption of Ikkbeta. Science 293, 1673-1677 (2001).
Lamhamedi-Cherradi, S.E. et al. Transcriptional regulation of type I diabetes by NF-kappa B. J Immunol 171, 4886-4892 (2003).
Zhao, Y., Krishnamurthy, B., Mollah, Z.U., Kay, T.W. & Thomas, H.E. NF-kappaB in type 1 diabetes. Inflammation & allergy drug targets 10, 208-217 (2011).
Golks, A., Tran, T.T., Goetschy, J.F. & Guerini, D. Requirement for O-linked N-acetylglucosaminyltransferase in lymphocytes activation. Embo J 26, 4368-4379 (2007).
Yang, W.H. et al. NFkappaB activation is associated with its O-GlcNAcylation state under hyperglycemic conditions. Proc Natl Acad Sci U S A 105, 17345-17350 (2008).
Allison, D.F. et al. Modification of RelA by O-linked N-acetylglucosamine links glucose metabolism to NF-kappaB acetylation and transcription. Proc Natl Acad Sci U S A 109, 16888-16893 (2012).
Ramakrishnan, P., Kahn, D.A. & Baltimore, D. Anti-apoptotic effect of hyperglycemia can allow survival of potentially autoreactive T cells. Cell death and differentiation 18, 690-699 (2011).
Haltiwanger, R.S., Grove, K. & Philipsberg, G.A. Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene)amino-N-phenylcarbamate. The Journal of biological chemistry 273, 3611-3617 (1998).
Rexach, J.E. et al. Quantification of O-glycosylation stoichiometry and dynamics using resolvable mass tags. Nat Chem Biol 6, 645-651 (2010).
Gilmore, T.D. & Gerondakis, S. The c-Rel Transcription Factor in Development and Disease. Genes & cancer 2, 695-711 (2011).
Slawson, C. & Hart, G.W. O-GlcNAc signalling: implications for cancer cell biology. Nature reviews. Cancer 11, 678-684 (2011).
Abbadie, C. et al. High levels of c-rel expression are associated with programmed cell death in the developing avian embryo and in bone marrow cells in vitro. Cell 75, 899-912 (1993).
Gerondakis, S. et al. Unravelling the complexities of the NF-kappaB signalling pathway using mouse knockout and transgenic models. Oncogene 25, 6781-6799 (2006).
Bryan, R.G. et al. Effect of CD28 signal transduction on c-Rel in human peripheral blood T cells. Mol Cell Biol 14, 7933-7942 (1994).
Shapiro, V.S., Truitt, K.E., Imboden, J.B. & Weiss, A. CD28 mediates transcriptional upregulation of the interleukin-2 (IL-2) promoter through a composite element containing the CD28RE and NF-IL-2B AP-1 sites. Mol Cell Biol 17, 4051-4058 (1997).
Housley, M.P. et al. O-GlcNAc regulates FoxO activation in response to glucose. The Journal of biological chemistry 283, 16283-16292 (2008).
Bunting, K., Wang, J. & Shannon, M.F. Control of interleukin-2 gene transcription: a paradigm for inducible, tissue-specific gene expression. Vitamins and hormones 74, 105-145 (2006).
Kang, S.M., Tran, A.C., Grilli, M. & Lenardo, M.J. NF-kappa B subunit regulation in nontransformed CD4+ T lymphocytes. Science 256, 1452-1456 (1992).
Herold, K.C. Achieving antigen-specific immune regulation. The Journal of clinical investigation 113, 346-349 (2004).
Banerjee, D., Liou, H.C. & Sen, R. c-Rel-dependent priming of naive T cells by inflammatory cytokines. Immunity 23, 445-458 (2005).
Gerondakis, S. et al. Rel-deficient T cells exhibit defects in production of interleukin 3 and granulocyte-macrophage colony-stimulating factor. Proc Natl Acad Sci U S A 93, 3405-3409 (1996).

(56) References Cited

OTHER PUBLICATIONS

Hilliard, B.A. et al. Critical roles of c-Rel in autoimmune inflammation and helper T cell differentiation. The Journal of clinical investigation 110, 843-850 (2002).

Bunting, K. et al. Genome-wide analysis of gene expression in T cells to identify targets of the NF-kappa B transcription factor c-Rel. J Immunol 178, 7097-7109 (2007).

Roos, M.D. et al. Streptozotocin, an analog of N-acetylglucosamine, blocks the removal of O-GlcNAc from intracellular proteins. Proceedings of the Association of American Physicians 110, 422-432 (1998).

Martin, A.G., San-Antonio, B. & Fresno, M. Regulation of nuclear factor kappa B transactivation. Implication of phosphatidylinositol 3-kinase and protein kinase C zeta in c-Rel activation by tumor necrosis factor alpha. The Journal of biological chemistry 276, 15840-15849 (2001).

Liou, H.C. & Hsia, C.Y. Distinctions between c-Rel and other NF-kappaB proteins in immunity and disease. Bioessays 25, 767-780 (2003).

Xing, D. et al. O-GlcNAc modification of NFkappaB p65 inhibits TNF-alpha-induced inflammatory mediator expression in rat aortic smooth muscle cells. PloS one 6, e24021 (2011).

Gao, Y., Miyazaki, J. & Hart, G.W. The transcription factor PDX-1 is post-translationally modified by O-linked N-acetylglucosamine and this modification is correlated with its DNA binding activity and insulin secretion in min6 beta-cells. Archives of biochemistry and biophysics 415, 155-163 (2003).

Hiromura, M. et al. YY1 is regulated by O-linked N-acetylglucosaminylation (O-glcNAcylation). The Journal of biological chemistry 278, 14046-14052 (2003).

Ea, C.K. & Baltimore, D. Regulation of NF-kappaB activity through lysine monomethylation of p65. Proc Natl Acad Sci U S A 106, 18972-18977 (2009).

Isomura, I. et al. c-Rel is required for the development of thymic Foxp3+ CD4 regulatory T cells. The Journal of experimental medicine 206, 3001-3014 (2009).

O'Connell, R.M. et al. Lentiviral vector delivery of human interleukin-7 (hIL-7) to human immune system (HIS) mice expands T lymphocyte populations. PloS one 5, e12009 (2010).

Ramakrishnan, P. & Baltimore, D. Sam68 is required for both NF-kappaB activation and apoptosis signaling by the TNF receptor. Mol Cell 43, 167-179 (2011).

Rexach, J.E. et al. Dynamic O-GlcNAc modification regulates CREB-mediated gene expression and memory formation. Nat Chem Biol 8, 253-261 (2012).

Wells, L. et al. Mapping sites of O-GlcNAc modification using affinity tags for serine and threonine post-translational modifications. Molecular & cellular proteomics : MCP 1, 791-804 (2002).

Ramakrishnan, P., Wang, W. & Wallach, D. Receptor-specific signaling for both the alternative and the canonical NF-kappaB activation pathways by NF-kappaB-inducing kinase. Immunity 21, 477-489 (2004).

Schreiber, E., Matthias, P., Muller, M.M. & Schaffner, W. Rapid detection of octamer binding proteins with 'mini-extracts', prepared from a small number of cells. Nucleic acids research 17, 6419 (1989).

\* cited by examiner

A

B

US 9,696,296 B2

TARGETING C-REL O-GLCNACYLATION AND USES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to U.S. Provisional Application No. 61/757,985, filed Jan. 29, 2013. The priority application is incorporated herein by reference in its entirety.

STATEMENT REGARDING FEDERALLY SPONSORED R&D

This invention was made with government support under GM039458 awarded by the National Institutes of Health. The government has certain rights in the invention.

BACKGROUND OF THE INVENTION

Field of the Invention

The present application relates generally to NF-κB subunit c-Rel and c-Rel activation through O-GlcNAcylation. Methods for identifying compounds that regulate O-GlcNAcylation of c-Rel and methods for identifying compounds that block O-GlcNAcylation of c-Rel are provided.

Description of the Related Art

NF-κB is a pleiotropic, evolutionarily conserved transcription factor family, having multiple roles in cell survival, development, apoptosis, immunity and inflammatory responses. The NF-κB family is composed of five members that function as dimers: p65 (RelA), RelB, c-Rel, p50 (and its precursor p105) and p52 (and its precursor p100). NF-κB members are preformed proteins that reside, in basal state, mostly in the cytoplasm bound to inhibitory proteins of the IκB family. In general, activation occurs through a signal-induced phosphorylation and proteasome-mediated degradation of IκB. This releases the previously bound NF-κB, which translocates to the nucleus and activates transcription.

Because the NF-κB members are preformed proteins, their initial activation and activity is mainly regulated by post-translational modifications rather than induction of their synthesis. O-GlcNAcylation is a form of intracellular post-translational protein modification. It involves attachment of the monosaccharide N-acetylglucosamine to serine and threonine residues (O-GlcNAc), in nuclear and cytoplasmic proteins in multicellular eukaryotes. O-GlcNAcylation is a reversible process catalyzed by O-GlcNAc transferase (OGT) and O-GlcNAcase (OGA) mediating addition and removal of O-GlcNAc, respectively, giving rise to functional diversity of proteins. O-GlcNAcylation levels play an important role in many key cellular processes, and O-GlcNAcylation is essential for T cell function.

O-GlcNAcylation can be increased under hyperglycemic conditions and enhance NF-κB-dependent transcription. Both O-GlcNAcylation and NF-κB activation have been associated with experimental and clinical diabetes. Growing evidence supports a pivotal role for O-GlcNAcylation in the activation of NF-κB in B and T cells (Golks et al. *Embo J* 26:4368-4379 (2007)). Recently, regulation of NF-κB p65 by O-GlcNAc glycosylation has received some attention with the identification of the sites of modification and their role in influencing p65 function (Yang et al. *Proc Natl Acad Sci USA* 105:17345-17350 (2008); Allison et al. *Proc Natl Acad Sci USA* 109:16888-16893 (2012)).

Although both NF-κB and O-GlcNAcylation were discovered some 25 years ago, the role of this post-translational modification in regulating NF-κB subunits other than p65, remain largely uncharacterized. As discussed in detail below, it has now been discovered that O-GlcNAcylation of c-Rel is necessary for DNA binding and transactivation following T-Cell Receptor stimulation. Thus, inhibiting O-GlcNAcylation of c-Rel provides an effective way to decrease cytokine production and T cell function and ameliorate autoimmune response in conditions such as type-I diabetes.

SUMMARY OF THE INVENTION

In one aspect, methods and compositions for identifying compositions that can block c-Rel O-GlcNAcylation and/or inhibit expression of c-Rel-dependent genes are provided.

In several embodiments, methods of identifying one or more compositions that can inhibit O-GlcNAcylation of c-Rel are provided. Test compositions are analyzed for their ability to inhibit the attachment of N-acetylglucosamine to c-Rel, for example at serine 350. A composition that inhibits the attachment of N-acetylglucosamine to c-Rel is identified as an inhibitor of O-GlcNAcylation of c-Rel. In some embodiments, the attachment of N-acetylglucosamine to wild-type c-Rel is analyzed. In other embodiments the attachment of N-acetylglucosamine to mutant c-Rel is analyzed.

In some embodiments, methods of identifying compositions that inhibit expression of c-Rel-dependent NF-κB-related cytokines are provided. Test compositions may initially be analyzed for their ability to inhibit O-GlcNAcylation of c-Rel, for example at serine 350. Compositions may also be analyzed for the ability to inhibit c-Rel activity, such as expression of one or more c-Rel-dependent NF-κB-related cytokines in T cells, for example IL-2, IFNγ or GMCSF.

In some embodiments, methods are provided for inhibiting c-Rel activity, such as expression of one or more c-Rel-dependent genes. The methods may comprise administering a composition identified as an inhibitor of c-Rel O-GlcNAcylation to a cell and monitoring at least one marker of c-Rel activity, such as c-Rel-dependent gene expression. In some embodiments, the composition identified is administered to a cell from a patient. In some embodiments, the patient is a human.

In other embodiments, methods of treating an autoimmune disease or autoimmune disorder associated with c-Rel-dependent signaling are provided. In some methods a therapeutically effective amount of a compound identified as inhibiting O-GlcNAcylation of c-Rel at serine 350 is administered to a patient in need of such treatment. In some embodiments, the autoimmune disorder is type-1 diabetes. In some methods, one or more markers of c-Rel-dependent signaling are also monitored. These markers may be, for example, a cellular auto-immune response or expression of a c-Rel-dependent NF-κB-related cytokine, such as IL-2, IFNγ or GMCSF.

BRIEF DESCRIPTION OF THE FIGURES

FIG. 1A is a western blot showing that c-Rel was a major O-GlcNAcylated NF-κB protein in both B (Ramos) and T (Jurkat) lymphoblastoid cell lines. Cells were treated with N-acetylglucosamine and PUGNAc and O-GlcNAcylation of c-Rel was detected using anti-O-GlcNAc (RL2) antibody. The bottom panels show total level of c-Rel in the immunoprecipitate. B is a western blot showing O-Glc-NAcylation of c-Rel in a hyperglycemic concentration of glucose. The addition of PUGNAc further enhanced the O-GlcNAcylation of c-Rel. C is a western blot showing O-GlcNAcylation of c-Rel and p65 in primary splenocytes from mice. D is a western blot suggesting that O-GlcNAcylated c-Rel exists in a complex with p65 in the cytoplasm. O-GlcNAcylation of p65 was detected using anti-O-GlcNAc (RL2) antibody (left panel), c-Rel was shown to co-precipitate with p65 (middle panel), and p65 runs at a lower molecular weight than the O-GlcNAcylated band and c-Rel (bottom panel). The molecular weight is shown by the 75 kDa mark and the white dividing line separates c-Rel and p65 in the blot. E is a western blot showing c-Rel O-GlcNAcylation in human peripheral blood mononuclear (PBMC) cells, mouse EL4 T cells, and mouse HEK-293T cells. c-Rel was immunoprecipitated and detected using anti-O-GlcNAc antibody (top) and anti-c-Rel antibody (bottom) for each cell type. F is a western blot showing c-Rel's ability to bind wheat germ agglutinin, an O-GlcNAc binding lectin, in Jurkat and mouse embryonic fibroblast (MEF) cells. G is a western blot of a chemoenzymatic O-GlcNAc detection assay in Jurkat and Ramos cells. O-GlcNAc residues on proteins were chemoenzymatically labeled with biotin. c-Rel was immunoprecipitated and O-GlcNAc sugars were detected using streptavidin-HRP. The bottom panel shows total c-Rel in the reaction. H shows baculoviral expression of c-Rel and p65 with or without OGT in insect cells. I shows reverse immunoprecipitation of O-GlcNAcylated c-Rel using anti-O-GlcNAc antibody. Jurkat cells were treated with N-acetylglucosamine and PUGNAc and the O-GlcNAc immunoprecipitate was analyzed with anti-c-Rel and anti-SP1 antibodies.

FIG. 2A shows Ramos cells treated with either 0 mM, 5 mM or 30 mM glucose and 100 µM PUGNAc. Cell lysate was chemoenzymatically-labeled and immunoblotted for c-Rel. The bottom panel shows unmodified p65 in the lysate. B is a graph indicating the percentage of c-Rel O-GlcNAcylation based on the concentration of glucose. C shows collision-induced dissociation mass spectrometry (CID-MS) site mapping of immunoprecipitated c-rel digested with chymotrypsin. '#' represents glycosylated peptide fragments. D shows CID-MS site mapping of digested c-rel that was derivatized by beta-elimination/Michael addition (BEMAD) with 2-aminoethanethiol (2-AET) and subject to LC-MS. E is a western blot showing immunoprecipitation of wild-type c-Rel and its mutants, S349A and S350A in HEK-293T cells. c-Rel was immunoprecipitated and probed with anti-O-GlcNAc antibody. Lower panel shows uniform amounts of c-Rel in the immunoprecipitate. F shows a schematic representation of the structure of c-Rel. RHD-rel homology domain, NLS-nuclear localization signal, RID-rel inhibitory domain, TAD-transactivation domain, P-phosphorylation sites, and O-GlcNAc-O-GlcNAcylation site are pictured. G is the human c-Rel DNA sequence encompassing the O-GlcNAcylation site and its mouse counterpart. H is a western blot showing immunoprecipitation of OGT in wild-type and S350A mutant c-Rel overexpressed in HEK-293T cells. c-Rel was probed for co-precipitation. The bottom panels show overexpressed c-Rel and OGT level in the lysates. I shows immunoprecipitation of flag tagged wild-type and mutant c-Rel overexpressed with myc tagged wild-type c-Rel in HEK-293T cells. Anti-myc immunoprecipitate was probed with anti-FLAG to examine c-Rel dimer formation. The bottom panel shows the level of wild-type and mutant FLAG-c-Rel in the lysate.

FIG. 3A is a graph of c-Rel-induced reporter gene activation in HEK-293T cells. B is a graph of c-Rel transactivation function for wild-type and mutant c-Rel using a CD28RE luciferase reporter plasmid (luc) in Jurkat cells. C is a graph indicating that c-Rel O-GlcNAcylation is required for anti-CD3/CD28-induced c-Rel dependent transactivation. D is a western blot showing shRNA-mediated suppression of endogenous c-Rel in Jurkat T-REx cells. E is a graph showing c-Rel suppression compromised PMA/Ionomycin-induced IL-2 production. Cells were treated and IL-2 level in the culture supernatant was assayed by ELISA. F is a western blot showing stable cell clones treated with doxycycline inducibly expressing wild-type and non-GlcNAcylatable c-Rel with a FLAG tag under tetracycline regulated promoter control. Bottom panel shows phospholipase C gamma as loading control. G is a western blot showing FLAG c-Rel immunoprecipitated and probed with anti-O-GlcNAc and anti-FLAG antibodies after treatment with doxycycline, glucose, and PUGNAc in mutant and wild-type cells. H is a western blot showing in vivo phosphorylation of wild-type and mutant c-Rel. c-Rel was immunoprecipitated using anti-FLAG and analyzed after autoradiography. Bottom panel shows total amount of c-Rel in the sample.

FIG. 4A is a western blot where cytoplasmic (top) and nuclear (bottom) extracts of Jurkat T-REx clones expressing wild-type and mutant c-Rel were analyzed for c-Rel levels after stimulation with anti-CD3/CD28. B is a western blot where cells were induced and analyzed after treating with PMA/Ionomycin. PLCγ, Lamin and SP1 were used as loading controls. C is a western blot showing FLAG-c-Rel immunoprecipitated from cytoplasmic and nuclear extracts of Jurkat cells expressing wild-type c-Rel. Bottom panel shows total c-Rel in the sample. D is a gel shift assay analyzing DNA binding of Jurkat cell clones expressing wild-type and mutant c-Rel. Cells were induced with doxycycline and then treated with anti-CD3/C28. Nuclear extract was analyzed for binding to a CD28RE probe. Samples were incubated with anti-FLAG antibody for supershift and 100-fold excess of unlabeled probe for competition to determine specificity of the binding. OCT1 was used as a control for the binding reaction and its specificity was controlled by competition with unlabeled OCT1 probe. Bottom panels show the input amounts of wild-type and mutant FLAG-c-Rel in the reaction. SP1 was used as the loading control. E is a gel shift assay showing mutations of the CD28RE region completely abolished the binding of the protein complexes to the CD28RE probe. F shows a western blot of cells treated overnight with 6-diazo-5-oxo-L-norleucine (DON), which is known to lead to inhibition of O-GlcNAcylation. G is a gel shift assay performed the same as FIG. 4D showing increased DNA binding by the enhancement of O-GlcNAcylation following PUGNAc and high glucose treatment. H is a gel shift assay where cells were treated as in FIG. 4D and DNA binding to IL-2κB probe was examined. I shows an In vitro oligonucleotide binding assay where cells were treated as in FIG. 4D and nuclear extract protein was assessed for binding to biotin labeled CD28RE oligonucleotide. The complex was precipitated with streptavidin agarose beads and probed with anti-FLAG antibody. Bottom panels show wild-type and mutant FLAG-c-Rel and SP1 as loading control in the nuclear extract.

FIG. 5A-B are graphs showing inhibition of O-GlcNAc cycling enhances c-Rel activity. PUGNAc increases anti-CD3/CD28-induced c-Rel dependent gene expression in Jurkat cells. Data (+/−SEM) is mean of triplicates from one of the three independent experiments. C-G are graphs showing expression of IL-2, GMCSF, IFNγ, IκBα, and A20 in Jurkat T-REx cell clones expressing wild-type and mutant c-Rel treated with PUGNAc and anti-CD3/C28. H is a graph showing expression of GMCSF in cells treated overnight with Streptozotocin (STZ), another OGA inhibitor that promotes O-GlcNAcylation. Quantitative real time PCR (qPCR) was performed at least in three independent experiments in triplicates and the relative levels of indicated genes were calculated with respect to the expression of transferrin receptor. Statistical significance was determined by two-tailed unpaired Student's t test and represented as mean±SEM.

FIG. 6A-D are graphs showing NF-κB-dependent gene expression in cells treated with TNF, which has been shown previously to activate c-Rel function. E is a western blot showing that high O-GlcNAcylation does not affect TNF-induced c-Rel activation, but it decreases p65 activation. F is a western blot showing that TNF stimulation did not induce O-GlcNAcylated c-Rel in cytoplasmic and nuclear extracts in Jurkat cells. G is schematic models of the regulation of c-Rel DNA binding and transactivation by O-GlcNAcylation: 1. TCR stimulation induces c-Rel DNA binding and gene induction by the wild-type protein that undergoes O-GlcNAcylation at serine 350; 2. Mutation of the O-GlcNAcylation site, serine 350, blocks TCR-induced DNA binding and gene expression; 3-4. Mutation of serine 350 has no effect on TNF-induced gene expression.

FIG. 7A is a western blot of cells treated as in FIG. 1. The lysate after c-Rel immunoprecipitation, was re-precipitated with anti-p65 antibody and probed with anti-O-GlcNAc and anti-p65 antibodies. B is gel shift assay of total cell lysates from Jurkat, Ramos and MEF cells treated as indicated in FIG. 1 and probed with anti-O-GlcNAc antibody (CTD110.6) to detect major O-GlcNAcylated proteins in the cell.

FIG. 8 is a gel shift assay after Coomassie blue staining of immunoprecipitated c-Rel. 400×10$^6$ Jurkat cells were treated with 30 mM glucose and 100 μM PUGNAc, immunoprecipitated with anti-c-Rel antibody and separated through a polyacrylamide gel. The c-Rel band was excised and analyzed by mass spectrometry.

FIG. 9 is a western blot of lysate from EL4 cells transiently transfected by nucleofection (Lonza) with pcDNA3 vector, FLAG tagged wild-type c-Rel and mutant c-Rel. 24 hrs later, cells were treated with anti-CD3/C28 for 3 hrs. Total lysate, cytoplasmic and nuclear extracts were analyzed for FLAG-c-Rel expression. PLCγ and SP1 were used as loading controls. ns-Nonspecific band.

FIG. 10A-C show expression levels of indicated genes in the presence or absence of c-Rel. CD4+ T cells were isolated from wild-type and c-Rel knockout mouse splenocytes and treated as indicated in FIG. 4. The expression levels of the indicated genes were calculated with respect to the expression of UBE2D2. Each gene was analyzed in triplicates by quantitative real time PCR. Statistical significance was determined by two-tailed unpaired Student's t test, and represented as mean±SEM.

FIG. 11A-D show graphs of the effect of mutant c-Rel on various mRNA expression levels. Jurkat T-REx cell clones expressing wild-type and mutant c-Rel were induced with doxycycline for 22 hrs. A-B show basal levels of indicated genes with and without c-Rel induction that were analyzed by qPCR. C-D show cells treated overnight with PUGNAc and then treated with anti-CD3/C28 for 3 hrs. Expression of indicated genes was assessed by qPCR. c-Rel dependent genes, C40 and GADD45β, were not significantly induced by anti-CD3/CD28 stimulation.

FIG. 12 shows a western blot of ramos cells (30×10$^6$) treated and analyzed as in FIG. 6F. Bottom panel shows SP1 O-GlcNAcylation used as a positive control.

DETAILED DESCRIPTION OF CERTAIN EMBODIMENTS

Figure 1:
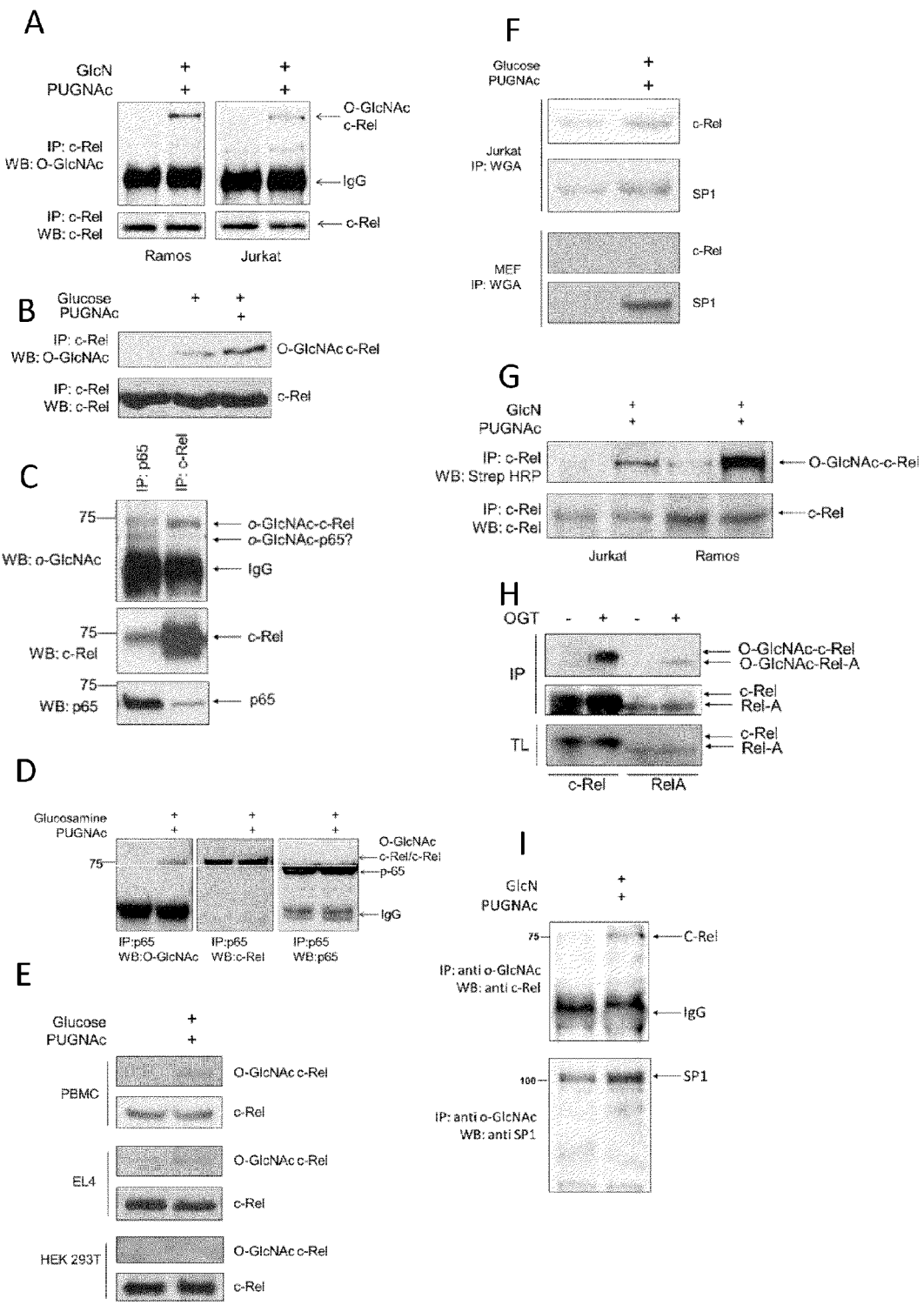
FIG. 1 shows NF-κB c-Rel is modified by O-GlcNAcylation.

Prior to this disclosure, c-Rel's role as the main site of O-GlcNAcylation for NF-κB was unknown. In addition, the ability of O-GlcNAcylation to effectively regulate activation and/or DNA binding of the c-Rel subunit had not been discovered. Activated c-Rel plays an important role in cytokine production. Thus, knowledge of the process by which c-Rel is O-GlcNAcylated allows a targeted approach to modulation of c-Rel activity, and therefore cytokine expression. The present disclosure identifies the serine 350 residue as the site of c-Rel O-GlcNAcylation. Screening for and identifying compositions capable of blocking O-GlcNAcylation of c-Rel at the serine 350 site can be used to provide compositions specifically tailored to regulating c-Rel function. Blocking O-GlcNAcylation of c-Rel's serine 350 residue may decrease autoimmune response, for example in conditions such as type I diabetes, by controlling the transactivation pathway responsible for over-reactive cytokine production. Thus, compounds that are able to block O-GlcNAcylation of c-Rel can have important therapeutic activities.

Applicants discovered that mutant c-Rel polypeptides which lack the serine 350 site for O-GlcNAcylation show decreased stimulation of expression of c-Rel-dependent genes, such as IL-2, IFNγ and GMCSF (Ramakrishnan et al., *Science Signaling*, * (2013), expressly incorporated herein by reference). In some embodiments, compositions that may be used for treating autoimmune disorders are identified by screening for compounds capable of blocking c-Rel activation, either by preventing binding at serine 350 or otherwise decreasing c-Rel O-GlcNAcylation. Compositions that may be identified as being useful for blocking c-Rel O-GlcNAcylation may include, for example and without limitation, small organic molecules, peptides and polypeptides, such as antibodies. In some embodiments cells are protected from over-active autoimmune response by contacting the cells with a compound identified as capable of blocking O-GlycNAcylation of c-Rel, such as by blocking binding of O-GlcNAc at serine 350.

In other embodiments, compounds identified by screening their ability to block O-GlcNAcylation of c-Rel, such as by blocking O-GlycNAcylation of serine 350 can be used to decrease overactive T cell function or suppress autoimmunity.

These and other embodiments are described in more detail below.

DEFINITIONS

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

"c-Rel" refers broadly to the c-Rel protein subunit of NF-κB, including mutant and variant forms as well as native forms. The NCBI reference IDs for human c-Rel are NM_002908.2 (mRNA) and NP_002899.1 (protein). The NCBI reference IDs for mouse c-Rel are NM_009044.2 (mRNA) and NP_033070.2 (protein). These sequences are incorporated herein by reference.

"Mutant c-Rel" refers to c-Rel protein which differs in some respect from the native sequence c-Rel protein. In some embodiments a mutant c-Rel protein has a sequence change which prevents glcNAcylation of the c-Rel subunit. This mutant may have a point mutation at the serine 350 residue of c-Rel.

As used herein, unless indicated otherwise the terms "inhibitor" and "c-Rel O-GlcNAcylation inhibitor" are used to refer to any composition, such as any molecule or compound, that blocks, inhibits, or reduces, either partially or fully, O-GlcNAcylation of c-Rel. Such inhibitors can, as a result of their activity, inhibit downstream effects that are mediated by O-GlcNAcylated c-Rel, such as T cell function, cytokine production, and autoimmune response regulated by cytokine production. In some embodiments c-Rel O-GlcNAcylation inhibitors may act directly on c-Rel, such as by specifically inhibiting binding at the serine 350 residue. In some embodiments c-Rel O-GlcNAcylation inhibitors may act indirectly, or non-specifically, such as by decreasing levels of O-GlcNAc that may available to modify c-Rel. C-Rel O-GlcNAcylation inhibitors may include, but are not limited to, small organic and inorganic molecules, nucleic acids, proteins, peptides, peptide mimetics and antibodies. In some embodiments a c-Rel inhibitor is a polypeptide, such as an antibody, that prevents c-Rel from being O-GlcNAcylated. In some embodiments a c-Rel inhibitor reduces the ability of O-GlcNAc transferase to add O-GlcNAc to c-Rel. In some embodiments a c-Rel inhibitor may be a molecule that reduces or prevents O-GlcNAcylation of serine 350 of c-Rel. For example, an inhibitor may be an antibody that binds to c-Rel and blocks access to serine 350. Examples of compositions and methods for inhibiting c-Rel O-GlcNAcylation and c-Rel's downstream activities are described below. Inhibition of c-Rel can be accomplished by providing a single c-Rel inhibitor, or by providing a combination of two or more c-Rel inhibitors.

"Biological property" or "biological activity" is a biological function, such as a biological function that may be caused by or mediated by c-Rel, a c-Rel O-GlcNAcylation inhibitor, or other composition. Biological properties of c-Rel includes TCR-induced DNA binding and activation of NF-κB dependent pathways, including activation of cytokine production. With regard to the c-Rel O-GlcNAcylation inhibitors, biological activity refers, in part, to the ability to inhibit O-GlcNAcylation of c-Rel. In some embodiments other biological activities of c-Rel O-GlcNAcylation inhibitors may include inhibition of binding of GlcNAc to the c-Rel serine 350 residue, inhibition of O-GlcNAc transferase, inhibition of NF-κB dependent gene transcription and the ability to regulate and preferably reduce or eliminate autoimmune responses in certain autoimmunity disorders.

The term "antibody" is used herein in the broadest sense and specifically covers human, non-human (e.g. murine) and humanized monoclonal antibodies, including full length monoclonal antibodies, polyclonal antibodies, multi-specific antibodies, and antibody fragments, including intrabodies, so long as they exhibit a desired biological activity. Antibodies exhibit binding specificity to a specific antigen.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, "treatment" is a clinical intervention made in response to and/or in anticipation of a disease, disorder or physiological condition manifested by a patient. The aim of treatment includes the alleviation or prevention of symptoms, slowing or stopping the progression or worsening of a disease, disorder, or condition and/or the remission of the disease, disorder or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

In the methods of the present invention, the term "control" and grammatical variants thereof, are used to refer to the prevention, partial or complete inhibition, reduction, delay or slowing down of an unwanted event.

In some embodiments, methods are provided for identifying compositions that inhibit, reduce, or prevent c-Rel O-GlcNAcylation, for example by blocking O-GlcNAcylation of serine 350 of c-Rel. In some embodiments, methods are provided for identifying compositions that reduce production of c-Rel dependent cytokines. In some embodiments methods are provide that protect cells from over-activation of autoimmune function or over-production of c-Rel-dependent cytokines. Screening assays to identify compositions are well known in the art and can be adapted to the disclosed methods.

Identifying Compositions that can Inhibit O-GlcNAcylation of c-Rel

In some embodiments, methods are provided for identifying a composition that can inhibit O-GlcNAcylation of c-Rel. In some embodiments, one or more compositions that are to be tested are provided. The compositions are then tested for their ability to inhibit the attachment of N-acetylglucosamine to c-Rel. In some embodiments, compositions are tested for their ability to inhibit attachment of N-acetylglucosamine to serine 350 of c-Rel. Compositions that inhibit the attachment of N-acetylglucosamine to c-Rel are identified as inhibitors of O-GlcNAcylation of c-Rel.

In some embodiments, the compositions that are tested for their ability to act as inhibitors in accordance with the present application include, but are not limited to, small molecules, nucleic acids, proteins, peptides, antibodies and fragments thereof, and other organic compounds, such as peptidomimetics, peptoids, and polyamides. The compositions can include, but are not limited to, soluble peptides, including members of random peptide libraries (see e.g., Lam, K. S. et al., 1991, Nature 354:82-84; Houghten, R. et al., 1991, Nature 354:84-86), and combinatorial chemistry-derived molecular libraries made of D- and/or L-configuration amino acids, phosphopeptides (including, but not limited to members of random or partially degenerate, directed phosphopeptide libraries; see e.g., Songyang, Z. et al., 1993, Cell 72:767-778), antibodies (including, but not limited to, polyclonal, monoclonal, humanized, anti-idiotypic, chimeric or single chain antibodies, and FAb, F(abN)$_2$ and FAb expression library fragments, and epitope-binding fragments thereof), and small organic or inorganic molecules, including libraries thereof. Other compositions that may be identified as inhibitors in accordance with the present application include, but are not limited to, small organic molecules.

Libraries of known compounds, including natural products or synthetic chemicals, and biologically active materials, including proteins, can be screened for compounds, which are inhibitors of c-Rel O-GlcNAcylation.

Small molecules may have the ability to act as inhibitors or activators of c-Rel O-GlcNAcylation and thus may be screened for such activity. Small molecules preferably have a molecular weight of less than 10 kD, more preferably less than 5 kD and even more preferably less than 2 kD. Such small molecules may include naturally-occurring small molecules, synthetic organic or inorganic compounds, peptides and peptide mimetics. However, small molecules in the present application are not limited to these forms. Extensive libraries of small molecules are commercially available and a wide variety of assays are well known in the art to screen these molecules for the desired activity.

In some embodiments, more than one composition is screened at a time.

In some embodiments compositions are specifically screened for their ability to block O-GlcNAcylation of serine 350 of c-Rel.

In some embodiments, the compositions identified as inhibiting attachment of N-acetylglucosamine to c-Rel specifically block the interaction of O-GlcNAc and the serine 350 residue of c-Rel. For example, in some embodiments, a composition is identified as blocking the interaction of O-GlcNAc and serine 350 by binding to c-Rel at or close to the serine 350 residue. In other embodiments a composition identified as inhibiting attachment of N-acetylglucosamine to c-Rel may work non-specifically. For instance, some known inhibitors of O-GlcNAcylation such as Don, Benzyl 2-acetamido-2-deoxy-α-D-galactopyranoside (BADGP), Alloxan, or Azaserine may be tested for their ability to inhibit O-GlcNAcylation of c-Rel and identified as inhibitors of c-Rel GlcNAcylation.

In some embodiments, compositions may be tested in vitro for their ability to inhibit O-GlcNAcylation of c-Rel by introducing the composition into cell culture under conditions in which O-GlcNAcylation of c-Rel is known to occur. Binding of O-GlcNAc to c-Rel can be determined using an appropriate assay as can be determined by the skilled artisan. In some embodiments, binding of O-GlcNAc to c-Rel can be determined using an immunoassay, for example as described below or as otherwise known to those skilled in the art. Compositions that decrease the amount of O-GlcNAcylation of c-Rel are identified as inhibitors of c-Rel O-GlcNAcylation.

In some embodiments C-Rel O-GlcNAcylation may be measured, for example, by immunoprecipitation using an anti-O-GlcNAc antibody, for example, RL2 and western blotting with an anti-c-Rel antibody, or vice versa. A decrease in O-GlcNAcylated c-Rel precipitated from cell culture after treatment with the test composition compared to cells not exposed to the test compound indicate the test composition's ability to inhibit O-GlcNAcylation of c-Rel. In some instances, cells may be treated prior to introduction of the test compound to enhance conditions leading to c-Rel O-GlcNAcylation, for example as described below.

In some embodiments, cells expressing c-Rel, such as Jurkat or Ramos cells, may be treated with N-acetylglucosamine, either in the presence or absence of one or more test compositions. C-Rel is then immunoprecipitated and O-GlcNAcylation analyzed by western blotting using an anti-O-GlcNAc antibody. In some embodiments a pathophysiologically meaningful hyperglycemic concentration of glucose (such as 30 mM) and/or the addition of an OGA inhibitor such as PUGNAc can be used to enhance O-GlcNAcylation.

Several other exemplary assays that may be used are described in the examples below, including a WGA binding assay and a chemoenzymatic O-GlcNAc labeling and detection assay (See Example 1). Briefly, in some embodiments cells expressing c-Rel, such as Jurkat or Ramos cells, are treated with N-acetylglucosamine in the presence and absence of one or more test compositions. A composition to enhance O-GlcNAcylation may be provided, such as an OGA inhibitor or glucose. In a WGA binding assay, cells are lysed and the lysate cleared and treated with succinylated wheat germ agglutinin (WGA). The immunoprecipitate is separated on a gel and c-Rel is detected using a specific antibody. The amount of c-Rel can be compared in the presence and absence of the test composition, with a decrease in the amount of c-Rel indicating that the test composition is an inhibitor of O-GlcNAcylation of c-Rel. In a chemoenzymatic O-GlcNAc labeling and detection assay cells are lysed and proteins precipitated and labelled, such as with an Click-IT O-GlcNAc enzymatic labeling system (Invitrogen). Labeled samples are precipitated and detected, for example by western blotting using an anti-streptavidin-HRP antibody. Again, a decrease in the amount of c-Rel relative to a control indicates that the test composition is an inhibitor of O-GlcNAcylation of c-Rel.

In some embodiments, testing of compositions for their ability to inhibit attachment of N-acetylglucosamine to serine 350 of c-Rel may comprise measuring the amount of O-GlcNAcylation at serine 350 in the presence of one or more test compositions. If the binding of O-GlcNAc to c-Rel at serine 350 is blocked or reduced in the presence of a test composition, the test composition is identified as having the ability to inhibit attachment of N-acetylglucosamine to serine 350 of c-Rel. In some embodiments an anti-O-GlcNAc antibody, for example RL2 or CTD110.6, may be used to measure the amount of O-GlcNAcylation at serine 350 of wild-type c-Rel in the presence of one or more test composition. In other embodiments, O-GlcNAcylation at serine 350 can be measured by performing wheat germ agglutinin (WGA) binding assays, radioactive sugar labeling assays, in vitro O-GlcNAc labeling assays, or in vitro mass tag labeling assays using compounds such as, for example, polyethyleneglycol. In some embodiments the amount of O-GlcNAcylation may be compared to the O-GlcNAcylation of mutant c-Rel with a point mutation at residue 350 in the presence of the test composition, as well as to O-GlcNAcylation of wild-type c-Rel. In some embodiments, direct binding of O-GlcNAc to the serine 350 residue can be determined by mass spectrometry or surface plasmon resonance.

As discussed above, in some embodiments, after c-Rel is contacted with O-GlcNAc in the presence of one or more test compositions, c-Rel can be isolated using, for example, an anti-c-Rel antibody. Antibodies useful for isolating c-Rel can be any antibody which recognizes the c-Rel peptide. All O-GlcNAcylated c-Rel peptides may be identified using, for example, an anti-O-GlcNAc antibody. In some embodiments, one or more of the antibodies can be attached to a surface, such as, for example, a bead, a column, an array, a glass slide, a microtiter plate, or a resin. In some embodiments an immobilized antibody can be used to isolate a particular test composition that binds to c-Rel and inhibits O-GlcNAcylation.

In some embodiments, multiple test compositions are screened simultaneously. For example a pool of test compounds can be screened for its ability to modulate binding of O-GlcNAc to c-Rel. If reduced activity is observed, the pool can be divided and subdivided to determine the particular test compound responsible for reduced binding of O-GlcNAc to c-Rel.

In some embodiments compositions that bind to c-Rel can be identified prior to testing the compositions for their ability to inhibit O-GlcNAcylation. In some embodiments, one or more test compositions can be attached to a surface such as a glass slide or microtiter plate. The test compositions can be present in the form of an array. Binding of the c-Rel to the immobilized test compositions can be identified, for example, using an antibody to c-Rel, fluorescence, luminescence, Western blotting, surface Plasmon resonance, or other known methods.

In some embodiments the ability of a test composition to bind at or near serine 350 of c-Rel can be determined. Binding of a test compound to c-Rel at serine 350 may be assessed using, for example, using known methods, such as by an immunoassay or surface plasmon resonance. If a test compound binds to c-Rel, and/or to serine 350, the test compound can be further tested to determine whether it can inhibit the O-GlcNAcylation of c-Rel. If O-GlcNAcylation is inhibited, the test compound may be further screened to determine whether it can inhibit downstream biological activity of c-Rel, such as the ability of c-Rel to signal transcription of c-Rel-dependent cytokines, such as by measuring the amount of one or more cytokines, for example IL-2, IFNγ, or GMCSF.

In some embodiments, a wild-type c-Rel is employed when identifying a compound that can inhibit O-GlcNAcylation of c-Rel. In other embodiments, a mutant c-Rel may be used when testing compounds for their ability to inhibit the attachment of N-acetylglucosamine to c-Rel, for example at serine 350 of c-Rel. In some embodiments, the mutant c-Rel may have a mutation that inhibits O-GlcNAcylation of the serine 350 residue of c-Rel, for example by altering the serine 350 binding site. In some instances, a mutant c-Rel may be used as a control to confirm that a test compound that prevents O-GlcNAcylation of wild-type c-Rel is targeting the serine 350 residue of c-Rel. For example, a compound that inhibits O-GlcNAcylation in wild-type c-Rel by forming a complex with c-Rel at the serine 350 residue may not be able to form a complex with a mutant c-Rel that has an altered serine 350 binding site.

Testing may be performed in vivo as well as in vitro in cell culture. Potential cell lines for testing in vitro may include B lymphoblastoid cell lines, a T lymphoblastoid cell lines, primary splenocytes and peripheral blood mononuclear cells. One skilled in the art would appreciate and understand how to perform methods of in vivo testing for potential inhibitors of O-GlcNAcylation of c-Rel. In some embodiments, testing for inhibitors may be performed by administering potential inhibitors to a subject, such as mouse or human subject. In some embodiments, the functional effect of potential inhibitors in a subject may be measured by whole genome microarrays or RNA sequencing assays. A cytokine profiling of blood samples from a subject may also be performed to study whether there are differences in gene expression, which may indicate inhibited c-Rel O-GlcNAcylation. In some embodiments, cytokine profiling may be performed using total blood cells or specific cell types. In some embodiments the specific cell types are lymphocytes, monocytes, granulocytes, or any combination of these cell types. Other in vivo assays may include studies of T lymphocyte proliferation and B lymphocyte antibody production.

As mentioned above, testing may also be performed under conditions that enhance O-GlcNAcylation. For instance, testing may be performed in hyperglycemic conditions. Conditions that enhance O-GlcNAcylation may also be created by inhibiting O-GlcNAcase. For example, O-GlcNAcase may be inhibited with PUGNac.

Once a compound is identified as able to bind c-Rel and/or able to inhibit the O-GlcNAcylation of c-Rel, the test compound can be tested for its ability to inhibit additional activities of c-Rel. For example, the ability of the test compound to prevent c-Rel DNA binding and/or c-Rel-dependent cytokine production, such as production of cytokines including, but not limited to, IL-2, IFNγ, or GMCSF, can be measured. Levels of these cytokines may be assessed by measuring their mRNA levels through, for example, PCR-based assays. Alternatively, levels of c-Rel-dependent cytokines may be measured by assessing their relevant protein levels through assays such as ELISA or western blot-based assays. mRNA or protein levels may be measured before and after exposure to a test compound to determine if the test compound has resulted in a decrease in c-Rel-dependent cytokine production. Alternatively, levels of anti-CD3/CD28-induced c-Rel binding to a CD28RE DNA probe, or binding to another DNA probe specific to a promoter region associated with a c-Rel-dependent cytokine may be measured before and after test compound exposure for a similar evaluation of change in cytokine transcription.

Although primarily focused on identifying compositions that inhibit O-GlcNAcylation of c-Rel, in some embodiments, testing may be performed to identify compositions that enhance O-GlcNAcylation of c-Rel. The assays described above may be adapted accordingly by the skilled artisan. Such testing may be performed under conditions that inhibit O-GlcNAcylation in order to test for compounds that enhance O-GlcNAcylation. For instance, testing may be performed in hypoglycemic conditions. Conditions that inhibit O-GlcNAcylation may also be created by enhancing O-GlcNAcase.

Identifying Compositions that Inhibit Expression of c-Rel-Dependent NF-κB-Related Cytokines In some embodiments, compositions that inhibit O-GlcNAcylation of c-rel are tested for their ability to inhibit expression of c-Rel-dependent NF-κB-related cytokines.

Briefly, one or more test compositions are provided to be tested. The compositions may have been previously identified as inhibiting O-GlcNAcylation of c-Rel. However, in some embodiments one or more of the test compositions may have been previously identified as able to bind to c-Rel. The provided test compositions are assayed for their ability to inhibit expression of c-Rel-dependent NF-κB-related cytokines, for example in T cells.

In some embodiments, the ability of a test composition to inhibit expression of c-Rel-dependent NF-κB-related cytokines is determined by measuring the expression of one or more of IL-2, IFNγ, GMCSF, or any combination of these cytokines. In some embodiments, quantitative PCR is used to measure expression, for example as described in Example 5 below. In some embodiments, conditions may be provided that are known to increase the amount of c-Rel O-glcNAcylation, such as hyperglycemic conditions.

In some embodiments cells expressing c-Rel, such as Jurkat or Ramos cells, are treated with a test composition. O-GlynAcylation may be promoted, for example with an OGA inhibitor such as PUGNAc or streptozotocin, or by mimicking hyperglycemic conditions. Cytokine gene expression may be enhanced by treatment of the cells with anti-CD3/CD28. Cytokine gene expression is analyzed, for example by quantitative real time PCR or other method known in the art. In some embodiments RNA is prepared from the cells and cDNA synthesized. Quantitative real time PCR is carried out and the results normalized.

If the amount of cytokine expression is decreased in the presence of the test composition, such as a previously identified inhibitor of O-GlcNAcylation of c-Rel, compared to a control sample, the test composition is considered to be able to inhibit the expression of these cytokines.

In some embodiments, anti-CD3/CD28-induced CD28RE binding to nuclear extracts associated with these cytokines may be measured, where a decrease in binding indicates a decrease in cytokine transcription.

In some embodiments, in vivo treatment with potential inhibitors of NF-κB-related cytokines may be performed. One skilled in the art would appreciate and understand how to perform methods of in vivo testing for potential NF-κB-related cytokine inhibitors. In some embodiments, testing for inhibitors may be performed by administering potential inhibitors to a subject, such as mouse or human subject. In some embodiments, the functional effect of potential inhibitors in a subject may be measured by whole genome microarrays or RNA sequencing assays. A cytokine profiling of blood samples from a subject may also be performed to study whether there are differences in gene expression, which may indicate NF-κB-related cytokine inhibition. In some embodiments, cytokine profiling may be performed using total blood cells or specific cell types. In some embodiments the specific cell types are lymphocytes, monocytes, granulocytes, or any combination of these cell types. Other in vivo assays may include studies of T lymphocyte proliferation and B lymphocyte antibody production.

In some embodiments, the compositions that may be tested as inhibitors of c-Rel-dependent NF-κB-related cytokine expression include, but are not limited to, small molecules, nucleic acids, peptides, antibodies and fragments thereof, and other organic compounds (e.g., peptidomimetics). The compounds can include, but are not limited to, soluble peptides, including members of random peptide libraries (see e.g., Lam, K. S. et al., 1991, Nature 354:82-84; Houghten, R. et al., 1991, Nature 354:84-86), and combinatorial chemistry-derived molecular libraries made of D- and/or L-configuration amino acids, phosphopeptides (including, but not limited to members of random or partially degenerate, directed phosphopeptide libraries; see e.g., Songyang, Z. et al., 1993, Cell 72:767-778), antibodies (including, but not limited to, polyclonal, monoclonal, humanized, anti-idiotypic, chimeric or single chain antibodies, and FAb, F(abN)$_2$ and FAb expression library fragments, and epitope-binding fragments thereof), and small organic or inorganic molecules, including libraries thereof. Other compounds that may be identified as inhibitors in accordance with the present application include, but are not limited to, small organic molecules.

Libraries of known compounds, including natural products or synthetic chemicals, and biologically active materials, including proteins, can be screened for compounds which are inhibitors of c-Rel-dependent NF-κB-related cytokine expression.

Small molecules may have the ability to act as inhibitors or activators of c-Rel-dependent NF-κB-related cytokine expression and thus may be screened for such activity. Small molecules preferably have a molecular weight of less than 10 kD, more preferably less than 5 kD and even more preferably less than 2 kD. Such small molecules may include naturally-occurring small molecules, synthetic organic or inorganic compounds, peptides and peptide mimetics. However, small molecules in the present application are not limited to these forms. Extensive libraries of small molecules are commercially available and a wide variety of assays are well known in the art to screen these molecules for the desired activity.

In some embodiments, the compounds identified as inhibitors may block O-GlcNAcylation of residue serine 350 of c-Rel.

In some embodiments, suitable test compounds are identified by testing for inhibition of O-GlcNAcylation of serine 350 of c-Rel. In some aspects, testing for inhibition of O-GlcNAcylation of serine 350 of c-Rel is performed in a B lymphoblastoid cell line, a T lymphoblastoid cell line, primary splenocytes or peripheral blood mononuclear cells. Testing may be performed under conditions that enhance O-GlcNAcylation. For instance, testing may be performed in hyperglycemic conditions. Conditions that enhance O-GlcNAcylation may also be created by inhibiting O-GlcNAcase. In one embodiment, O-GlcNAcase is inhibited with PUGNAc.

Inhibiting Expression of c-Rel-Dependent Genes

In some embodiments, the invention relates to methods of inhibiting expression of c-Rel-dependent genes by administering an inhibitor of c-Rel O-GlcNAcylation to a cell and monitoring at least one marker of c-Rel-dependent gene expression. In some embodiments, the inhibitor of c-Rel O-GlcNAcylation is Don, Benzyl 2-acetamido-2-deoxy-α-D-galactopyranoside (BADGP), Alloxan, or Azaserine.

In some embodiments, the inhibition is performed in vivo. In some embodiments, the inhibition is performed in vitro. In some embodiments, the inhibition is performed ex vivo. In some embodiments, the cell is from a cell line, is grown in cell culture, or is derived from a biological sample. In some embodiments, the cell is a B lymphoblastoid cell line, a T lymphoblastoid cell line, primary splenocytes or peripheral blood mononuclear cells. In some embodiments, the cell is from a patient. In some aspects, the patient is a mammal, such as a human. c-Rel is inhibited in the cell, as described above.

In some embodiments, the inhibitor is an antibody, nucleic acid, small molecule, protein, or other entity as described above. In some embodiments, the c-Rel O-Glc-NAcylation inhibitor blocks O-GlcNAcylation of serine residue 350 of c-Rel.

In some embodiments, markers of c-Rel-dependent gene expression are monitored in the cell, one or more clones of the cell, one or more cells from the same population as the cell, or a biological sample derived from the same organism as the cell. Monitoring of markers of c-Rel-dependent gene expression may be used to determine whether the cell exhibited activation of the c-Rel-dependent gene expression pathway, and whether inhibition of c-Rel resulted in a reduction in markers of c-Rel-dependent gene expression relative to a control cell or clone of the cell that did not receive an inhibitor.

In some embodiments, the marker of c-Rel-dependent gene expression comprises a cellular auto-immune response, such as increased survival of self-reactive T cells. In some embodiments, the marker of c-Rel-dependent gene expression comprises expression of a c-Rel-dependent NF-κB-related cytokine. In some aspects, the NF-κB-related cytokine is IL-2, IFNγ or GMCSF. In some embodiments, markers may include other NF-κB-related genes that have been concurrently affected due to c-Rel down-regulation.

In other embodiments, conditions are modified to enhance O-GlcNAcylation so that the effect of the inhibitor may be measured. For example, increasing the glucose concentration a cell is exposed to, or otherwise simulating diabetic conditions, may enhance c-Rel O-GlcNAcylation. An inhibitor's effectiveness may be assessed by determining if there is a reduction in one or more markers of c-Rel-dependent expression, as discussed above.

In some embodiments, in vivo inhibition of c-Rel O-GlcNAcylation may be performed. One skilled in the art would appreciate and understand how to perform methods of in vivo analysis of potential c-Rel O-GlcNAcylation inhibitors. In some embodiments, inhibition of c-Rel O-GlcNAcylation may be performed by administering potential inhibitors to a subject, such as mouse or human subject. In some embodiments, the functional effect of the inhibitors in a subject is measured by whole genome microarrays or RNA sequencing assays. A cytokine profiling of blood samples from a subject may also be performed to study differences in gene expression. In some embodiments, cytokine profiling is performed using total blood cells or specific cell types. In some embodiments the specific cell types are lymphocytes, monocytes, granulocytes, or any combination of these cell types. Other in vivo assays may include studies of T lymphocyte proliferation and B lymphocyte antibody production.

Methods of Treatment

In other embodiments, the invention relates to methods of treating an autoimmune disease or autoimmune disorder associated with c-Rel-dependent signaling by administering a therapeutically effective amount of a compound identified as inhibiting O-GlcNAcylation of c-Rel, such as a compound that inhibits O-GlcNAcylation of c-Rel at serine 350, to a patient identified to be in need of such treatment. In some embodiments, a patient is first identified as suffering from or likely to suffer from an autoimmune disorder. In some embodiments, the autoimmune disorder is type-1 diabetes. In other embodiments, the patient is identified as suffering from or likely to suffer from an autoimmune or inflammatory disease or disorder such as juvenile or rheumatoid arthritis, psoriasis, lupus, celiac disease, inflammatory bowel disease, or sclerosing cholangitis. Other potential diseases and disorders are also known that may be associated with c-Rel-dependent signaling, including diseases and disorders associated with NF-κB-related signaling. (See, e.g., http://www.bu.edu/nf-kb/physiological-mediators/diseases/for diseases associated with activation of NF-κB and specific references for each listed disease.)

In some embodiments, the method of treating a patient further includes the step of monitoring markers of c-Rel-dependent signaling. Potential markers of c-Rel-dependent signaling include IL-2, IFNγ, and GMCSF. One skilled in the art will appreciate that a patient with a disease associated with activation of c-Rel-dependent signaling will exhibit c-Rel-dependent cytokines. One skilled in the art will also appreciate that c-Rel-dependent cytokines or other NF-kB-dependent genes may be indicative of a disease associated with c-Rel-dependent signaling. (See, e.g., http://www.bu.edu/nf-kb/gene-resources/target-genes/for NF-kB-dependent genes that may be monitored as markers of c-Rel-dependent signaling.)

In some embodiments, c-Rel is inhibited in at least one cell of the patient, using the methods described above. In some embodiments, a therapeutically effective amount of c-Rel inhibitor is administered to the patient. In some embodiments, all substantial c-Rel expression or function is inhibited. In some embodiments, c-Rel expression or activity is reduced, but is not completely inhibited.

In some embodiments, a diagnosis is performed on the patient to determine whether the patient is in need of treatment to inhibit c-Rel-dependent signaling. In some embodiments, the diagnosis comprises monitoring at least one marker of c-Rel-dependent signaling, for example, monitoring for an increased presence of some NF-κB-related cytokines compared to healthy individuals. In some embodiments, the presence of a certain symptoms associated with NF-κB activation in autoimmune diseases indicates the patient is in need of treatment to inhibit c-Rel-dependent signaling. In some embodiments, the absence of a marker indicates the patient is in need of treatment to inhibit c-Rel-dependent signaling. In some embodiments, the increase of a marker indicates the patient is in need of treatment to inhibit c-Rel-dependent signaling. In some embodiments, the decrease of a marker indicates the patient is in need of treatment to inhibit c-Rel-dependent signaling. For example, levels of IL-2 protein may be measured, or levels of IL-2 transcript may be measured. For example, levels of IL-2 protein may be measured by immunoblotting, ELISA, immunoprecipitation, flow cytometry, or immunohistochemistry. For example, levels of IL-2 transcript may be identified by northern blotting, microarray analysis, or RT-PCR.

EXAMPLES

The following examples, including the experiments conducted and results achieved, are provided for illustrative purposes only and are not to be construed as limiting upon the present invention.

Example 1

NF-κB c-Rel is O-GlcNAcylated Both In Vitro and In Vivo

This example illustrates modification of NF-κB c-Rel by O-GlcNAcylation.

Materials and Methods

Reagents and Antibodies.

Glucose, N-acetylglucosamine, Streptozotocin, DON, Phorbol 12-myristate 13-acetate (PMA), Ionomycin, Blasticidin, Doxycyline and poly (dI-dC) were purchased from Sigma. Zeocin was from Invivogen. PUGNAc (O-(2-acet-amido-2-deoxy-D-glucopyranosylidene)amino-N-phenyl-carbamate) was from Toronto Research Chemicals. Recombinant TNF was from Peprotech. [32P] Orthophosphate and [32P] γATP were from Perkin Elmer Radiochemicals. IL-2 ELISA kit and antibodies against mouse CD3ε (145-2C11) and C28 (37.51) were from Biolegend. Antibodies against human CD3 (OKT3) and C28 (clone 28.2) were from eBioscience. Antibodies against c-Rel, p65, SP1, OGT, Actin, PLCγ and Lamin were from Santa Cruz Biotechnology. Anti-FLAG was from Sigma. Anti-O-GlcNAc antibodies, RL2 was from Abcam and CTD110.6 were from Covance.

Cells and Animals.

Jurkat, Jurkat T-REx, Ramos, EL-4, MEF and 293-T cells were grown as previously described (Ramakrishnan et al., *Cell death and differentiation* 18:690-699 (2011)). Human peripheral blood mononuclear cells (PBMC) were purchased from Allcells. The tetracycline-inducible Jurkat T-REx cells were purchased from Invitrogen. c-Rel knock-out mice were kindly provided by Dr. Hsiou-Chi Liou, Weill Medical College of Cornell University, New York, USA. C57BL/6 mice were from a colony maintained in-house. Mice were housed in the California Institute of Technology animal facility and handled in accordance with National Institute of Health guidelines under Institutional Animal Care and Use Committee approved protocols. All mice used were 6-10 weeks old unless otherwise indicated.

Immunoprecipitations and Western Blotting.

Total cell lysates were prepared and immunoprecipitations and western blotting were performed as described (Ramakrishnan et al., *Mol Cell* 43:167-179 (2011)). Human peripheral blood mononuclear cells (PBMC) were activated with PHA for 48 hrs. Mouse thymoma EL4 cells ($50\times10^6$) and HEK 293T cells ($10\times10^6$) were cultured overnight in 5 mM glucose medium. Cells were treated with 30 mM glucose and PUGNAc (100 μM) for 3 hrs. c-Rel was immunoprecipitated and detected using anti-O-GlcNAc antibody and anti-c-Rel antibody for each cell type (FIG. E). For the immunoprecipitation of transiently expressed proteins in HEK-293T cells, $2\times10^6$ cells were transfected by calcium phosphate precipitation method, lysed as above and immunoprecipitated using relevant antibodies.

WGA Binding Assay.

Jurkat and Ramos cells ($10\times10^6$) were cultured overnight in RPMI medium containing 5 mM glucose with and without 4 mM N-acetylglucosamine and 100 μM PUGNAc. Cells were lysed in the lysis buffer (50 mM HEPES (pH 7.9), 150 mM NaCl, 1% Triton X-100 and EDTA free protease inhibitor). The lysate was pre-cleared with protein A/G beads (Santacruz) and later incubated with succinylated wheat germ agglutinin (WGA) for 4 hrs at 4° C. WGA also binds to sialic acid and we used succinylated WGA to limit its binding to sialic acid and increase specificity for O-GlcNAc. The immunoprecipitate was separated on SDS-PAGE and c-Rel and SP1 as a control were detected using specific antibodies.

In Vitro Chemoenzymatic O-GlcNAc Labeling and Detection Assay.

Jurkat ($25\times10^6$) and Ramos cells ($30\times10^6$) were treated for 8 hrs with N-acetylglucosamine 4 mM and 100 μM PUGNAc. Cells were lysed in a buffer containing 20 mM HEPES (pH 7.9) and 1% SDS. Proteins were precipitated using methanol:chloroform and labeling reactions were performed using Click-IT O-GlcNAc enzymatic labeling system according to manufacturer's instructions (Invitrogen). Labeled samples were precipitated using methanol:chloroform:$H_2O$ and resuspended in buffer containing 50 mM Tris-HCl (pH 8.0) and 1% SDS and detected in western blotting using anti-streptavidin-HRP antibody.

Baculoviral expression. Baculovirus was produced by transfecting SF9 insect cells with pVL1393 vector encoding the gene of interest using lipofectamine reagent (Invitrogen). For co-infection, High Five insect cells were infected with OGT expressing virus and c-Rel or p65 expressing virus. Cells were harvested 60 hrs post infection and lysed on ice for 30 minutes in the lysis buffer (11 mM Sodium phosphate pH 7.4, 150 mM NaCl, 0.1% SDS, 0.5% Sodium deoxycholate, 1% Triton X-100 and 1× complete protease inhibitor cocktail). Proteins were immunoprecipitated from the lysate and detected using anti-O-GlcNAc (RL2) antibody.

Results

We examined NF-κB proteins in a variety of cellular systems for evidence of elevated O-GlcNAcylation and found that c-Rel was a major O-GlcNAcylated NF-κB protein in both B (Ramos) and T (Jurkat) lymphoblastoid cell lines (FIG. 1A).

Figure 7:
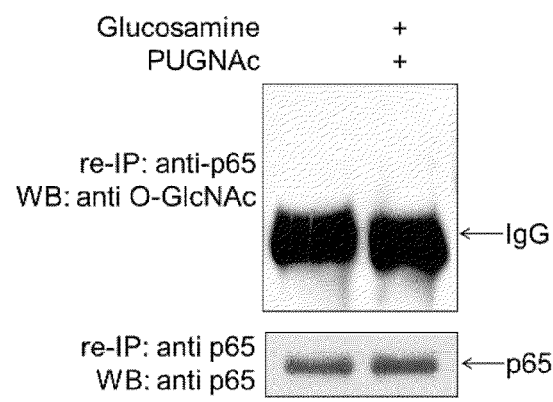
FIG. 7 shows reimmunoprecipitated p65 failed to show an O-GlcNAcylation signal even with elevation of global O-GlcNAcylation, suggesting c-Rel is the major O-GlcNAcylated protein in lymphocytes.
Figure 7:
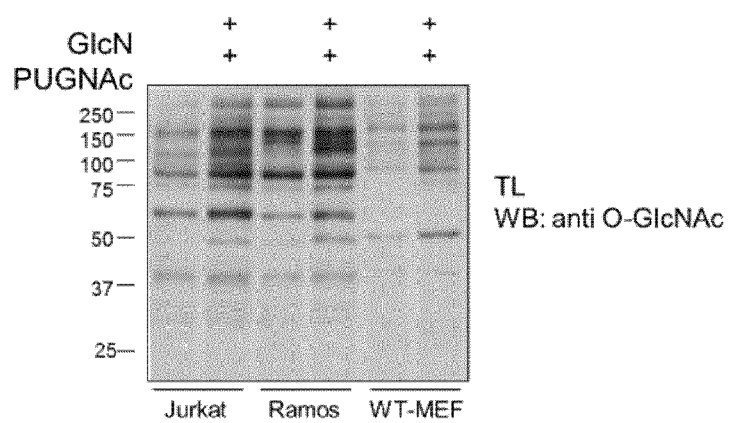

To enrich the O-GlcNAcylated pool of proteins, Ramos and Jurkat cells ($50\times10^6$) were treated with N-acetylglucosamine (GlcN, 4 mM), a precursor of GlcNAcylation, and to the OGA inhibitor, PUGNAc (100 μM) for 12 hrs. c-Rel was immunoprecipitated and O-GlcNAcylation was detected using anti-O-GlcNAc (RL2) antibody (FIG. 1A) O-GlcNAcylation of c-Rel was also detected in a pathophysiologically meaningful hyperglycemic concentration of glucose (30 mM) and addition of PUGNAc (100 μM) for 3 hrs further enhanced the O-GlcNAcylation of c-Rel in Jurkat cells (FIG. 1B). Under similar conditions, c-Rel was also found to be O-GlcNAcylated in C57BL/6 primary splenocytes from mice ($75\times10^6$) (FIG. 1C). Primary splenocytes were treated with N-acetylglucosamine and PUGNAc for 8 hrs, and NF-kB proteins, p65 and c-Rel were immunoprecipitated from the lysate and detected as indicated. O-GlcNAcylation of p65 in primary splenocytes was also at a modest level (FIG. 1C). Interestingly, O-GlcNAcylated c-Rel existed in a complex with p65 in the cytoplasm as indicated by their reciprocal co-precipitations (FIG. 1C-D). Unlike phosphorylation, O-GlcNAcylation does not change the electrophoretic mobility of proteins (Hart et al. *Annual review of biochemistry* 80:825-858 (2011)). The O-GlcNAcylated band in p65 immunoprecipitates appeared at a higher molecular weight region than that of p65, suggesting the O-GlcNAcylation of co-precipitated c-Rel (FIG. 1D). Furthermore, following depletion of c-Rel from the lysate, reimmunoprecipitated p65 failed to show an O-GlcNAcylation signal, suggesting c-Rel is the major O-GlcNAcylated protein in lymphocytes (FIG. 7A).

c-Rel O-GlcNAcylation was also found in peripheral blood mononuclear cells from humans as well as in the glucose-dependent mouse T cell line, EL4[31] (FIG. 1E). However, no O-GlcNAcylation of endogenous c-Rel was observed in epithelial cell lines, HEK-293T or mouse embryonal fibroblasts (FIGS. 1E and 1F bottom) and this was not due to a lack of elevation of global O-GlcNAcylation in these cells (FIG. 7B). c-Rel was also found to bind the O-GlcNAc binding lectin, wheat germ agglutinin (WGA), and its reactivity to lectin increased with glucosamine and PUGNAc treatment (FIG. 1F). Furthermore, a chemoenzymatic method to identify O-GlcNacylated proteins also showed O-GlcNAcylated c-Rel, both in Ramos and Jurkat cells (FIG. 1G). In vivo, both c-Rel and p65 were found O-GlcNAcylated in the heterologous baculoviral expression system following their co-expression with OGT (FIG. 1H). Finally, we could precipitate c-Rel from glucosamine and PUGNAc treated cells through an anti-O-GlcNAc antibody (FIG. 1I).

Example 2 c-Rel is O-GlcNAcylated at a Single Serine Residue (S350) in the REL Inhibitory Domain Materials and Methods Mutant c-Rel and Plasmids.

Human c-Rel and its mutants were cloned into pCMX vector with a myc tag for transient expression. The S349A and S350A mutants of c-Rel were generated by PCR based site directed mutagenesis. For inducible expression, wild-type and mutant c-Rel with a FLAG tag were cloned into pcDNA4 vector (Invitrogen). For baculoviral expression, c-Rel, p65 and OGT were cloned into the vector pVL1393 (AB vector).

In Vitro PEG Labeling.

Jurkat or Ramos cells were cultured overnight in RPMI medium containing 5 mM glucose. Cells were treated for 3 hrs with 30 mM glucose and 100 µM PUGNAc, lysed in boiling 1% SDS containing Complete™ protease inhibitor cocktail (Roche) and 100 µg of total protein was chemoenzymatically-labeled with a 5 kDa polyethylene glycol (PEG 5000) mass tag as described previously (Rexach et al., *Nat Chem Biol* 6:645-651 (2010)). The labeled lysate was separated on a 4-12% Bis-Tris polyacrylamide gel (Invitrogen) and immunoblotted with an anti-c-Rel antibody.

Mass Spectrometry.

Jurkat or Ramos cells ($4.5 \times 10^8$) cells were cultured overnight in 5 mM glucose. Cells were stimulated for 3 hrs with 30 mM glucose and 100 µM PUGNAc, lysed and immunoprecipitated using anti c-Rel antibody and separated in 4-12% Bis-Tris gel in MOPS buffer. c-Rel band was excised, manually digested with chymotrypsin, and analyzed by nanoLC-MS with CID and ETD fragmentation as previously described but with modifications. (Rexach et al. *Nat Chem Biol* 8:253-261 (2012).) Peptides were separated with a 120 min gradient and duplicate analyses were performed on an LTQ Orbitrap XL for accurate mass determination of precursor ions. A portion of the digested peptides was subject to Beta-elimination, Michael addition with 2-aminoethanethiol (2-AET). (Wells, L. et al. *Molecular & cellular proteomics: MCP* 1:791-804 (2002).) After 2 hours at 50° C., the reaction was quenched with acetic acid and organic solvents were removed by vacuum centrifugation. The sample was analyzed by nanoLC-MS on an LTQ Orbitrap XL as described above. Data was searched using Mascot allowing for variable modifications of 2-AET at Ser/Thr.

Results

Figure 2:
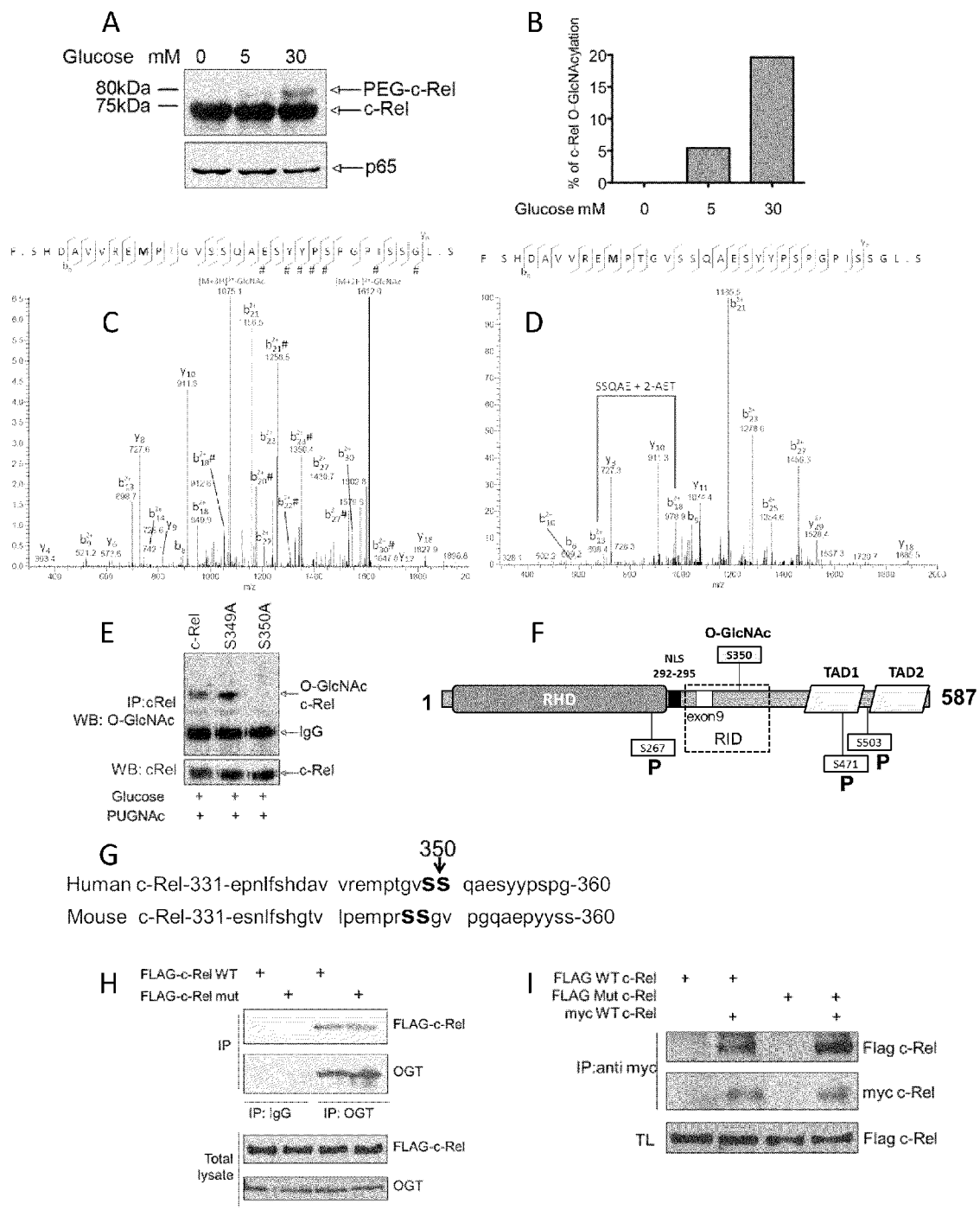
FIG. 2 shows O-GlcNAcylation of c-Rel at serine 350.

To identify the stoichiometry of c-Rel O-GlcNAcylation, we employed a chemoenzymatic approach for labeling O-GlcNAc residues with a polyethylene glycol (PEG5000) mass tag. (Slawson et al. *Nature reviews. Cancer* 11:678-684 (2011).) This approach increases the molecular weight of protein in increments of 5 kDa, depending on the number of O-GlcNAc moieties simultaneously attached to the protein. We found that following treatment with high glucose and PUGNAc, human c-Rel showed a shift of 5 kDa, which suggests that c-Rel is mono-O-GlcNAcylated. Interestingly, we saw a greatly increased proportion of O-GlcNAcylated c-Rel at 30 mM glucose compared to 5 mM glucose, suggesting that c-Rel glycosylation is both dynamic and inducible (FIG. 2A). We quantified the stoichiometry of O-GlcNAcylated c-Rel at 30 mM glucose by densitometry and found that approximately 20% of the total c-Rel was modified with O-GlcNAc (FIG. 2B).

Figure 8:
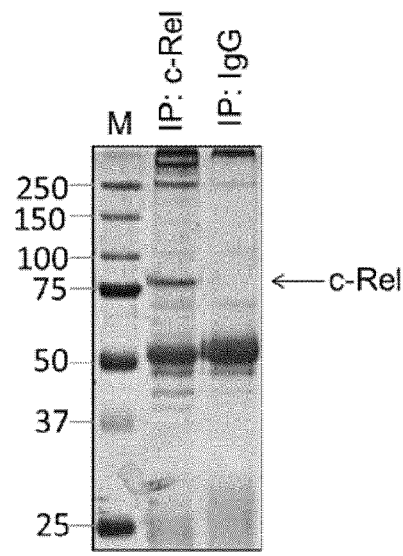
FIG. 8 shows immunoprecipitation of endogenous c-Rel for site mapping of O-GlcNAcylation.

To map the site of O-GlcNAcylation, endogenous c-Rel was immunoprecipitated from high glucose and PUGNAc treated Jurkat or Ramos cells (FIG. 8) and subjected to collision-induced dissociation mass spectrometry (CID-MS) and CID-MS following BEMAD (beta-elimination/Michael addition with 2-aminoethanethiol) derivatization. These experiments mapped O-GlcNAc glycosylation to 5349 or 5350 of human c-Rel (FIGS. 2C and 2D). We separately mutated the two serine residues to alanine and tested c-Rel O-GlcNAcylation following overexpression under hyperglycemic conditions. Unlike the endogenous c-Rel, overexpressed c-Rel was O-GlcNAcylated in HEK-293T cells. While the S349A mutant behaved just like the wild-type c-Rel, S350A mutation completely blocked O-GlcNAcylation of c-Rel (FIG. 2E). As shown in the diagram, serine 350 in c-Rel is located in its REL inhibitory domain (RID) (FIG. 2F). These two serine residues are also conserved in mouse c-Rel (FIG. 2G). Interestingly, serine 350 in c-Rel is in the same region as the O-GlcNAcylation site in p65, T352, suggesting conserved accessibility of this region for the OGT enzyme. Thus, in line with the PEG labeling data (FIG. 2A), we identified a single serine residue in c-Rel, 5350, as the O-GlcNAcylation site.

OGT enzyme is known to form complex with its substrates. Lack of O-GlcNAcylation in c-Rel S350A was not due to its inability to bind to OGT, because overexpressed wild-type c-Rel and its mutant were found to bind specifically to the endogenous OGT with similar efficiency (FIG. 2H). Moreover, the mutation did not interfere with the ability of c-Rel to form dimers indicating its competitiveness in protein-protein interactions that are crucial for NF-κB function (FIG. 2I). Cells had been lysed 24 hrs post-transfection and anti-myc immunoprecipitate was probed with anti-FLAG to examine c-Rel dimer formation.

Example 3

The S350A Mutation in c-Rel, while Blocking its O-GlcNAcylation and Transactivation, does not Affect TCR-Induced c-Rel Phosphorylation Materials and Methods Luciferase Reporter Plasmid Assays.

c-Rel was overexpressed in HEK-293T cells with luciferase reporter plasmids and assayed after 24 hrs. Wild-type and mutant c-Rel were overexpressed in Jurkat cells with the CD28RE luciferase reporter plasmid (luc) and assayed after 24 hrs. Wild-type and mutant c-Rel were transfected into Jurkat cells and 24 hrs later, cells were treated with plate bound anti-CD3/CD28 for 4 hours and luciferase activity was assessed using a dual luciferase assay system (Promega).

Statistical Analysis.

Difference in gene expression was statistically analyzed using two-tailed unpaired Student's t test with PRISM. Data are presented as mean±SEM, unless otherwise indicated. All the represented genes showed a p-value of <0.05. (Graphpad, La Jolla, Calif.).

shRNA and Lentiviral Transduction.

shRNA directed against 3' non-coding region of human c-Rel and LacZ as a non-specific control in a microRNA-155 based expression cassette was synthesized and then amplified by PCR with primers containing restriction sites. C-Rel and LacZ shRNA expression cassette were constructed. These cassettes were cloned into pHAGE6 lentiviral vector. (O'Connell et al. *PloS one* 5:2009 (2010).) For the selection of transduced cells, the extracellular domain of human CD271 was placed downstream of the shRNA cassette separated by an IRES sequence. Lentiviral expression plasmids expressing shRNA and helper proteins were transiently transfected into HEK-293T cells using TransIT-293 transfection reagent (Minis Bio). Culture supernatants were collected at 60 hours post-transfection and 100 times concentrated by ultracentrifugation in a SW28 rotor at 16,500 rpm for 90 minutes at 4° C. Virus was resuspended in RPMI media and 50 μl was used to infect $200 \times 10^3$ Jurkat cells/well in 6 well plates in the presence of 5 μg/ml polybrene. Cells were spun at 2500 rpm for 90 minutes at 30° C. to facilitate viral adherence to the cell surface, supernatant was discarded and cells were cultured in fresh medium. Cells were analyzed for sA-mediated suppression of c-Rel, 72-96 hours post infection.

Magnetic-Activated Cell Sorting (MACS) and Fluorescence-Activated Cell Sorting (FACS).

Jurkat cells transduced with lentivirus expressing shRNA c-Rel were selected for surface expression of CD271 by magnetic sorting using CD271 microbeads (Miltenyi Biotec) following the manufacturer's instructions. Cells were blocked using Fc Block reagent (anti-mouse CD16/32) (BD Biosciences) and CD271 expression was confirmed by FACS using FITC conjugated anti-CD271 antibody (Miltenyi Biotec) and analyzed using FACSCalibur flow cytometer (BD Biosciences, San Jose, Calif.) and FlowJo software (FlowJo, Ashland, Oreg.).

In Vitro CD3/CD28 Activation.

Jurkat cells were cultured at $1.5 \times 10^6$ cells/ml in 6-well plates or 10 cm plates in the presence of 1 μg/ml of Doxycycline for 22 hours for the induction of FLAG-c-Rel. Cells were stimulated for the indicated time points with plate bound anti-CD3 and anti-CD28 (2 μg/ml each). Cells ($75 \times 10^6$) were induced with doxycycline for 22 hrs, treated with PUGNAc for 12 hrs and glucose (30 mM) for 3 hrs. FLAG c-Rel was immunoprecipitated and probed with anti-O-GlcNAc and anti-FLAG antibodies.

In Vivo Orthophosphate Labeling.

Performed as described (Ramakrishnan et al., *Mol Cell* 43:167-179 (2011)). Wild-type and mutant c-Rel cells ($75 \times 10^6$) were induced with doxycycline as in 'C', starved for 90 minutes in phosphate free medium, and stimulated with anti-CD3/CD28 for 3 hrs in presence of radioactive phosphate. c-Rel was immunoprecipitated using anti-FLAG and analyzed after autoradiography.

Results

Figure 3:
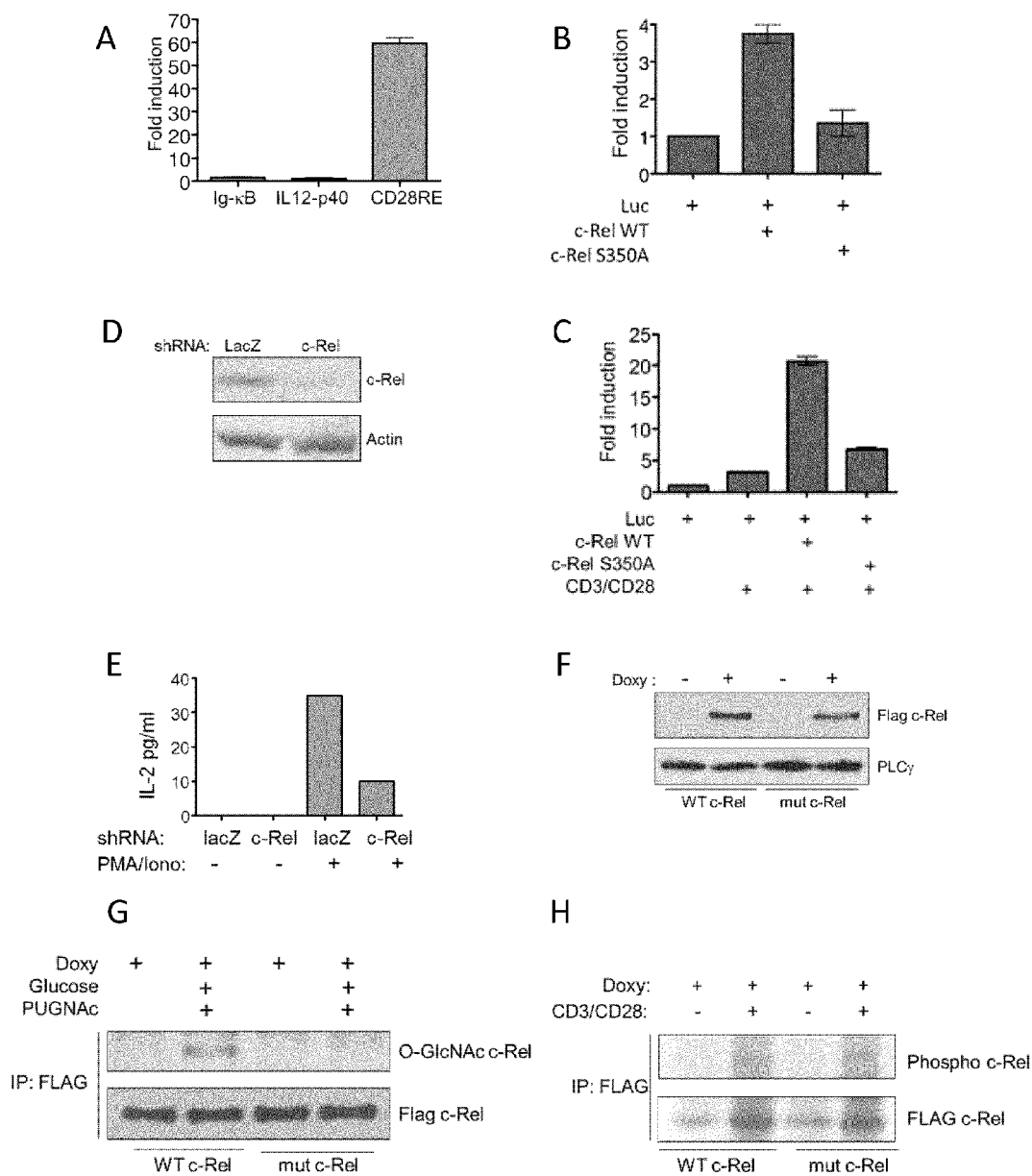
FIG. 3 shows that mutating c-Rel O-GlcNAcylation site regulates its activity, yet not phosphorylation.

To investigate the function of c-Rel O-GlcNAcylation, initially we relied on the transactivation potential of overexpressed c-Rel. In our assays, a luciferase reporter under CD28-responsive element (provided by Prof. Arthur Weiss) gave the maximum response to c-Rel-induced activation (FIG. 3A). Based on this, we chose to use anti-CD3/CD28 co-stimulation to study c-Rel function. We examined the impact of the S350A mutation on the transactivation function of c-Rel and found that this mutation greatly reduced the transactivating potential of overexpressed c-Rel (FIG. 3B), as well as that by anti-CD3/CD28 co-stimulation (FIG. 3C).

Our attempts to study the function of O-GlcNAc site-directed mutation in c-Rel by constitutive overexpression was encumbered by the fact that, as previously reported elevated c-Rel expression over a few days induced death of the transfected cells. To circumvent this problem, we turned to a tetracycline-inducible system to express c-Rel in Jurkat cells. First, to allow the cells to tolerate the induced c-Rel levels and to analyze the function of the mutant protein with minimum interference from the endogenous protein, we suppressed endogenous c-Rel expression by lentiviral delivery of an shRNA that targets the c-Rel 3' non-coding region. We achieved significant inhibition of c-Rel expression (FIG. 3D) and this resulted in a substantial reduction in PMA/Ionomycin-induced IL-2 production, which is dependent on c-Rel (FIG. 3E). IL-2 level in the culture supernatant was assayed by ELISA. Second, we generated stable cell clones inducibly expressing wild-type and non-GlcNAcylatable c-Rel with a FLAG tag under tetracycline regulated promoter control. Addition of the tetracycline analogue, doxycycline, induced detectable c-Rel expression at about 20-24 hours in these clones (FIG. 3F). We analyzed multiple clones to exclude clonal variation and verify the consistency of inducible c-Rel expression and anti-CD3/CD28 co-stimulation. Similar to overexpression experiments, the inducibly-expressed wild-type c-Rel was O-GlcNAcylated while the mutant c-Rel, though expressed at similar levels like the wild-type protein, showed a complete lack of O-GlcNAcylation (FIG. 3G).

Based on the previous studies, serine 350 in c-Rel is not known to undergo phosphorylation (Perkins, 2006). We examined c-Rel phosphorylation induced by CD28 co-stimulation, which has been previously shown to cause an increase in c-Rel level and its phosphorylation. We found no noticeable differences in phosphorylation status of inducibly expressed c-Rel or its mutant following anti-CD3/CD28 co-stimulation in an in vivo orthophosphate labeling assay (FIG. 3H).

Example 4

A Point Mutation at the O-GlcNAcylation Site in c-Rel Compromises its DNA Binding Ability Materials and Methods In Vitro CD3/CD28 Activation.

Jurkat cells were cultured at $1.5 \times 10^6$ cells/ml in 6-well plates or 10 cm plates in the presence of 1 μg/ml of Doxycycline for 22 hours for the induction of FLAG-c-Rel. Cells were stimulated for the indicated time points (3 hours) with plate bound anti-CD3 and anti-CD28 (2 μg/ml each). Cells were also induced and analyzed as described after treating with PMA/Ionomycin. PLCγ, Lamin and SP1 were used as loading controls. Cytoplasmic and nuclear extracts were also prepared after culturing in the presence of 1 μg/ml of Doxycycline for 22 hours for the induction of FLAG-c-Rel. FLAG-c-Rel was immunoprecipitated and analyzed with anti-O-GlcNAc antibody.

Electrophoretic Mobility Shift Assay (EMSA).

Nuclear protein extracts were prepared as described[7]. Nuclear extracts corresponding to 4-6 μg of protein were tested for DNA binding using the probes containing c-Rel binding CD28RE region and p65 binding IL2-κB region. OCT1 probe was used as a control. In the probe containing CD28RE-NF-IL-2B AP-1 region, the AP site was mutated as previously described to restrict the protein binding only to the CD28RE site in our assays. (Shapiro et al. *Mol Cell Biol* 17:4051-4058 (1997).) Lysates were incubated with [$^{32}$P] γATP labeled probe in the binding buffer (Tris-Cl 10 mM, pH 7.5, Nacl 50 mM, glycerol 4%, MgCl2 1 mM, EDTA 0.1 mM, poly(dI-dC) 50 μg/ml, and 0.1 mM DTT) for 20 min at room temperature. Antibody supershift assays to identify FLAG-c-Rel DNA binding was performed in ice for 30 min using 1 μg of anti-FLAG (M2) antibody. Samples were separated in 5% non-denaturing polyacrylamide gel and analyzed by autoradiography.

Oligonucleotide Pull Down Assay.

Wild-type and mutant c-Rel expressing cells (40×10$^6$) were cultured overnight in RPMI medium containing 1 µg/ml of doxycycline for 22 hours. Cells were stimulated with plate bound anti-CD3/CD28 for 3 hrs. Cytoplasmic extracts were prepared as described. (Schreiber et al *Nucleic acids research* 17:6419 (1989).) Nuclear extracts were prepared in a lysis buffer (0.1% NP-40, HEPES 20 mM, pH 7.9, NaCl 420 mM, MgCl2 1.5 mM, EDTA 0.2 mM, DTT 1 mM, Protease inhibitor cocktail), and were diluted in the above buffer without NaCl to reach a final concentration of 150 mM NaCl. Lysates containing approximately 200 µg of the nuclear proteins were incubated with 10 µg of poly (dI-dC) and 1 µg of annealed biotinylated CD28RE region containing oligonucleotides at 4° C. in a rotator. After 1 hr, streptavidin agarose beads were added to the mix for additional 3 hrs. The beads were washed thrice in a buffer containing 250 mM NaCl and analyzed by western blotting.

Results

Figure 4:
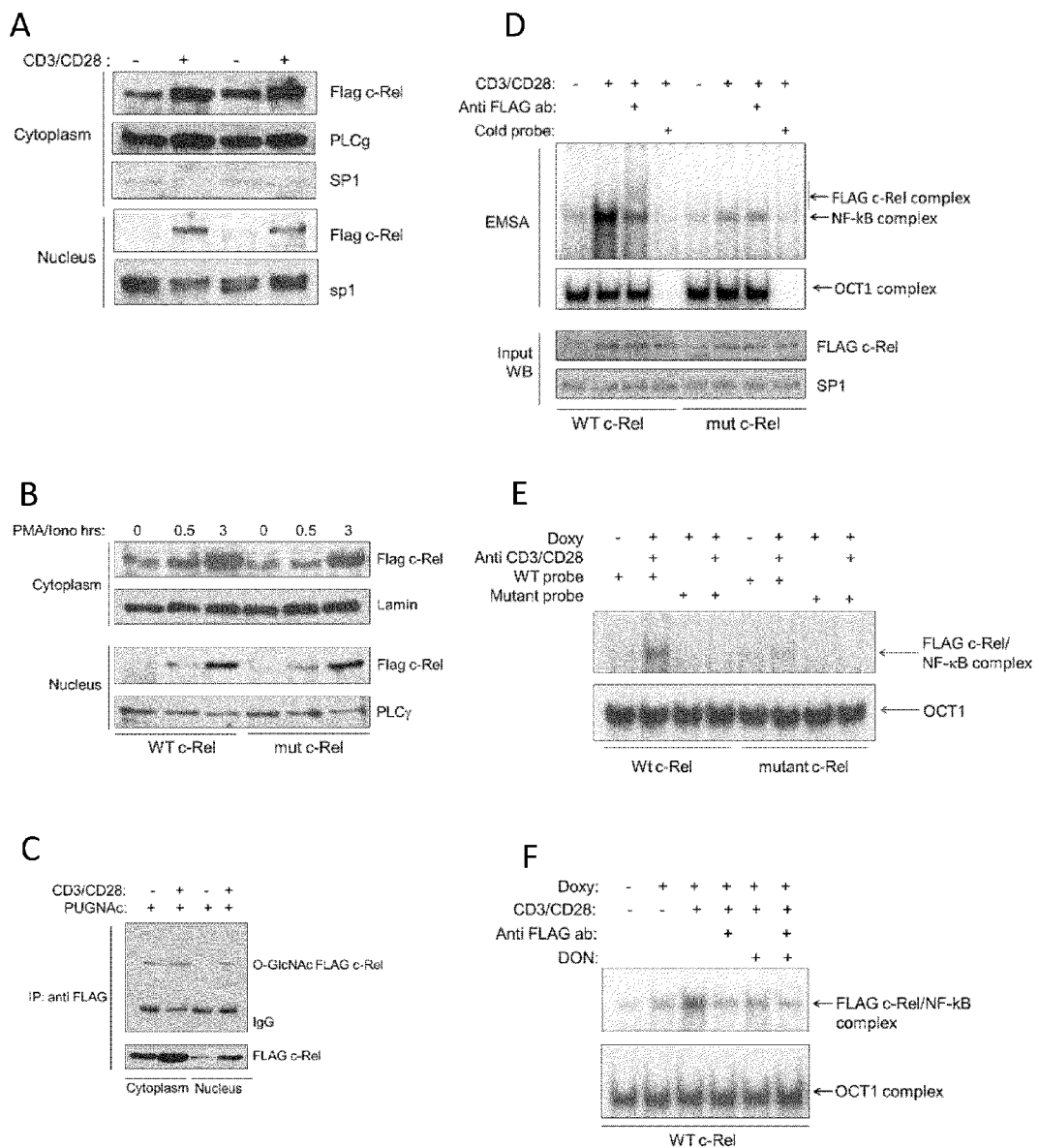
FIG. 4 shows mutation of the c-Rel O-GlcNAcylation site does not affect its nuclear translocation, but impairs its binding to CD28 responsive element.
Figure 4:
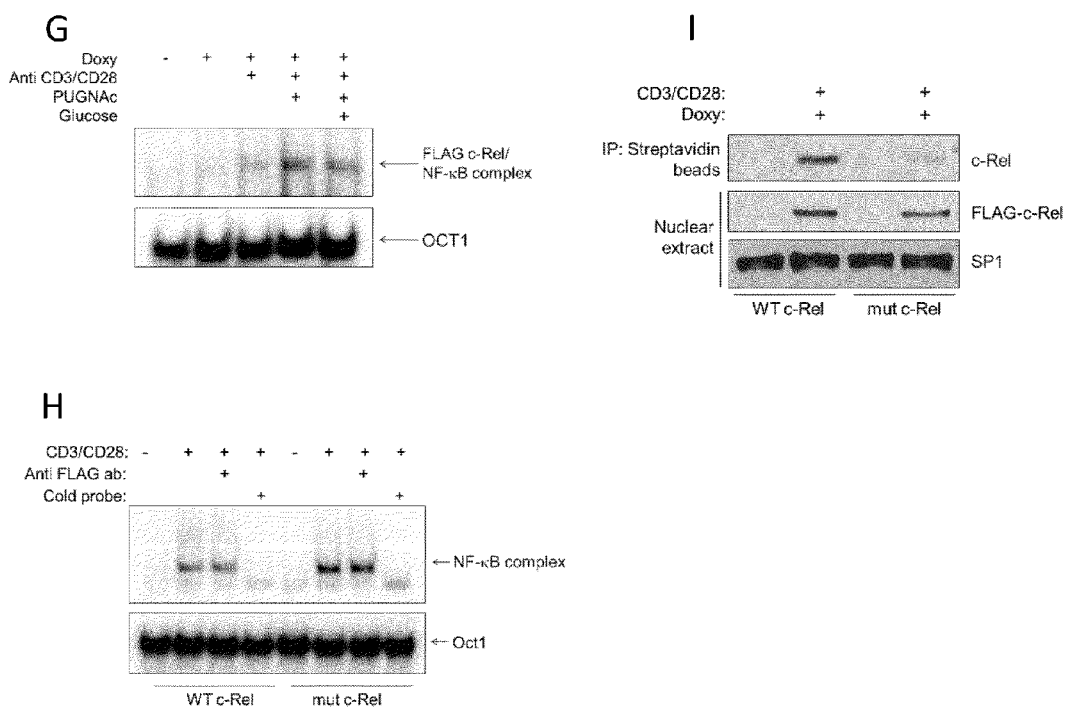
Figure 9:
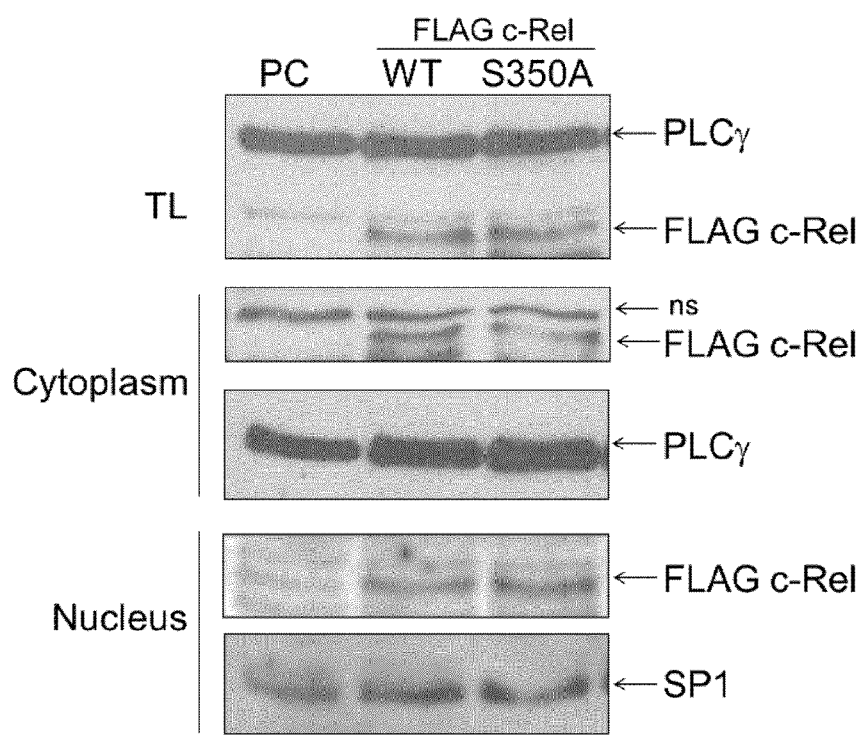
FIG. 9 shows that there is anti-CD3/CD28-induced nuclear translocation of mutant c-Rel, following its transient transfection into mouse EL-4 T cells.

To study nuclear translocation, we induced c-Rel expression in Jurkat cells, and then stimulated with anti-CD3/CD28. We analyzed the cytoplasmic and nuclear extracts and found comparable translocation of wild-type and mutant c-Rel into the nucleus (FIG. 4A). We further confirmed the anti-CD3/CD28-induced nuclear translocation of mutant c-Rel, following its transient transfection into mouse EL-4 T cells (FIG. 9). Treatment with PMA/Ionomycin, which activates the same downstream signaling components as anti-CD3/CD28 co-stimulation, also resulted in comparable nuclear translocation of wild-type and mutant c-Rel (FIG. 4B). We also found O-GlcNAcylated c-Rel in the nucleus of Jurkat cells following anti-CD3/CD28 stimulation, suggesting a nuclear role for the modified c-Rel (FIG. 4C).

Because nuclear translocation of mutant c-Rel was intact, next we examined its DNA binding to account for its compromised transactivation. We observed an anti-CD3/CD28-inducible increase in binding to the CD28RE probe with nuclear extracts from wild-type c-Rel expressing cells. Addition of anti-FLAG antibody to the binding reaction supershifted a portion of the complex, implying occupancy of the DNA by FLAG-c-Rel. In contrast, the nuclear extract from mutant c-Rel expressing cells showed significantly less anti-CD3/CD28 inducible DNA binding and no shifted complex in presence of anti-FLAG antibody. Both wild-type and mutant c-Rel complexes were competed out by the presence of a 100-fold excess unlabeled probe (FIG. 4D). OCT1 DNA binding competed with an OCT1 probe was used as a control for the gel shift assays. The differences in DNA binding observed were not due to a difference in the amount of the relevant protein in the nuclear extracts (FIG. 4D bottom panels). Mutations in the CD28RE region completely abolished the binding of the protein complexes to the probe indicating the specificity of the interaction (FIG. 4E).

Similar to non-GlcNAcylatable c-Rel, inhibition of O-GlcNAcylation by 6-diazo-5-oxo-L-norleucine (DON) treatment, decreased anti-CD3/CD28-induced CD28RE binding of nuclear extracts from wild-type c-Rel expressing cells (FIG. 4F). Conversely, this DNA binding was significantly increased by the enhancement of O-GlcNAcylation following PUGNAc and high glucose treatment further implying a role for O-GlcNAcylation of c-Rel in its DNA binding (FIG. 4G).

Maximal induction of IL-2 depends on multiple transcription factors including, c-Rel, p65, AP-1 and NFAT. To demonstrate that c-Rel O-GlcNAcylation specifically affects the CD28RE-dependent IL-2 transcription, we used the p65 binding region (IL2-κB) in the IL-2 promoter as a probe. Anti-CD3/CD28 inducible IL2-κB-DNA-protein complexes were formed both in wild-type and mutant c-Rel expressing samples, with a modest increase in DNA binding of the latter. These DNA bound complexes were not supershifted by anti-FLAG antibody indicating the absence of FLAG-c-Rel in their complexes (FIG. 4H). This result also demonstrates the efficient stimulation of both modified cell lines by TCR activation. To further validate the defective DNA binding of the S350A mutant c-Rel, we performed in vitro oligonucleotide pull-down assay. Consistent with the gel shift assays, the mutant c-Rel showed dramatically reduced binding to a biotinylated CD28RE probe (FIG. 4I).

Example 5 c-Rel O-GlcNAcylation Regulates the Expression of a Subclass of T Cell Receptor-Induced Genes Materials and Methods PUGNAc Cell Treatment Assays.

Jurkat cells were treated with PUGNAc (100 µM) for 12 hours and then treated with plate bound anti-CD3/CD28 (2 µg/ml) for 3 hours. Some cells were additionally treated overnight with Streptozotocin (STZ, 2 mM) prior to PUGNAc treatment. Gene expression was analyzed by quantitative real time PCR. In other cases, Jurkat T-REx cell clones expressing wild-type and mutant c-Rel were induced with doxycycline for 22 hrs, treated with PUGNAc overnight and then treated with anti-CD3/C28 for 3 hrs.

Quantitative Real Time PCR.

DNA-free RNA was prepared using the RNeasy Mini Kit according to the manufacturer's instructions (Qiagen). cDNA was synthesized from 0.5-1.0 µg total RNA using random hexamers (Promega) and Superscript III reverse transcriptase first-strand synthesis kit (Invitrogen, Carlsbad, Calif.). Quantitative real time PCR using cDNA corresponding to 20-60 ng of total RNA and Taqman Gene Expression Assays (Applied Biosystems, Foster City, Calif.) was performed in a Real-Time PCR machine (Realplex, Eppendorf) according to the manufacturer's instructions. The results obtained for individual genes were normalized to the expression of TFR for human genes and UBE2D2 for mouse genes. Quantitative real time PCR (qPCR) was performed at least in three independent experiments in triplicates and the relative levels of indicated genes were calculated with respect to the expression of transferrin receptor. Statistical significance was determined by two-tailed unpaired Student's t test and represented as mean±SEM.

Results

Figure 10:
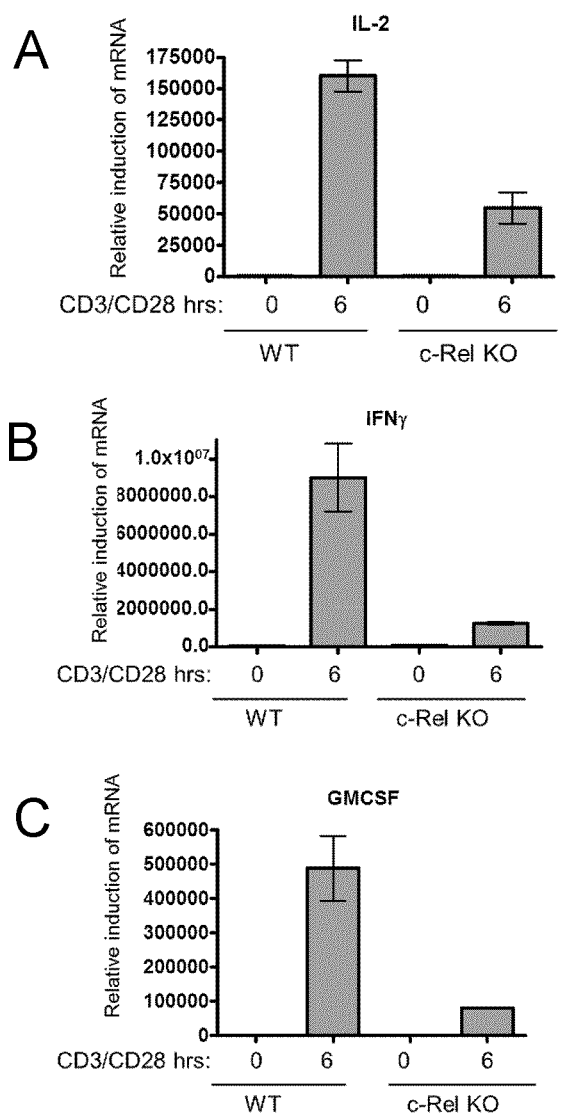
FIG. 10 shows IL-2, IFNγ and GMCSF are c-Rel dependent genes.
Figure 11:
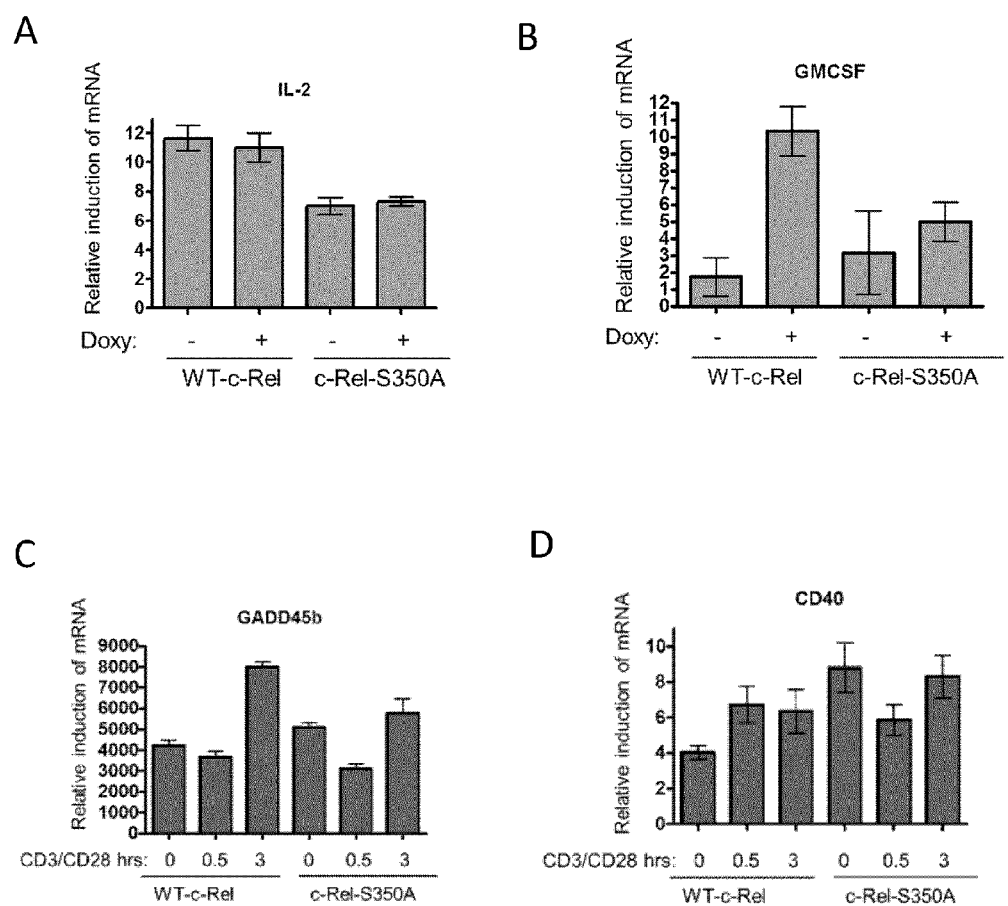
FIG. 11 shows expression of mutant c-Rel has no dominant negative effect.

TCR activation mediates autoimmune T-cell responses in hyperglycemic conditions like diabetes. We studied anti-CD3/CD28 co-stimulation for TCR activation that induces several c-Rel dependent genes including genes for IL-2, IFNγ and GMCSF. We confirmed using c-Rel knockout T cells that these genes are indeed under c-Rel regulation (FIG. 10). Substantiating the requirement of O-GlcNAcylation for the transactivation function of c-Rel (FIG. 3B-C), exposure to PUGNAc significantly potentiated anti-C3/C28-induced expression of IL-2 and GMCSF (FIG. 5A,B).

Figure 5:
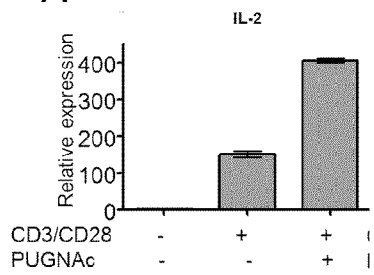
FIG. 5 shows c-Rel O-GlcNAcylation is required for TCR-induced CD28RE-dependent gene expression.
Figure 5:
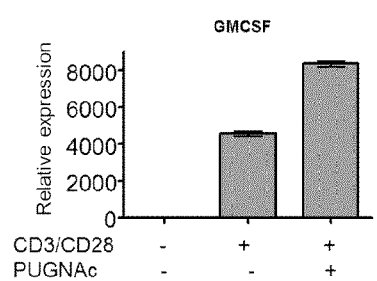
Figure 5:
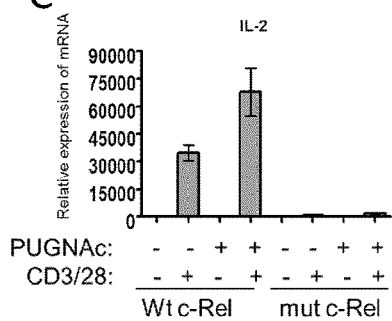
Figure 5:
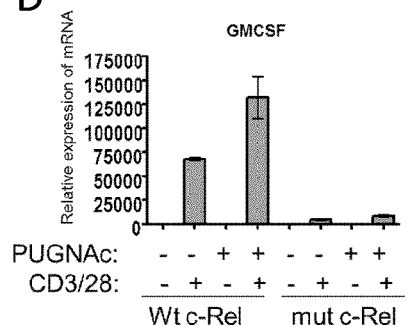
Figure 5:
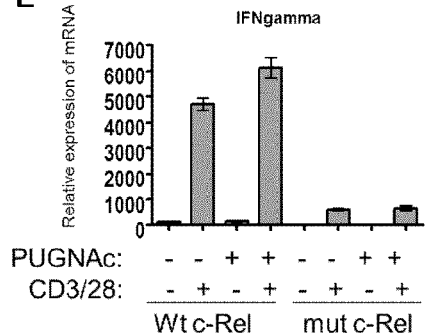
Figure 5:
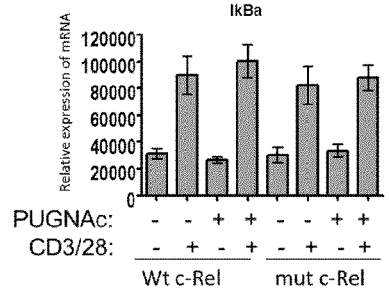
Figure 5:
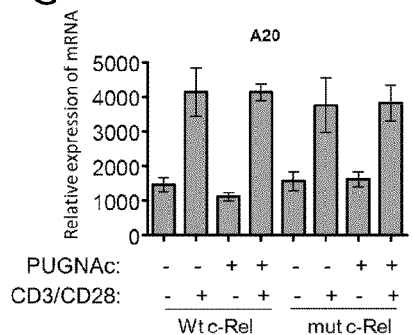
Figure 5:
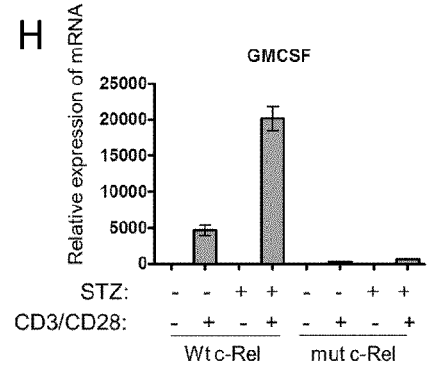
Figure 6:
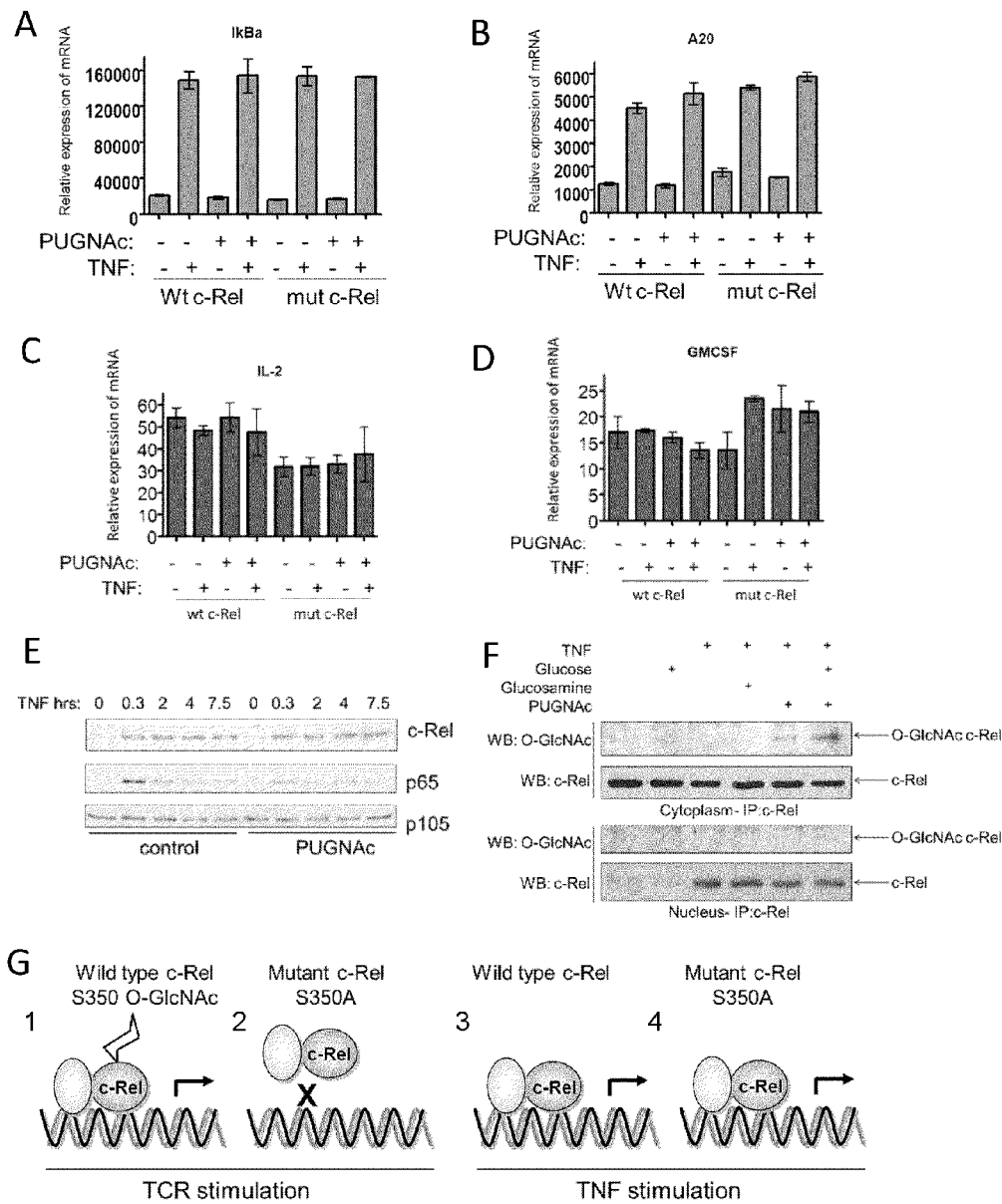
FIG. 6 shows TNF-induced gene expression and c-Rel activation is independent of c-Rel O-GlcNAcylation.

Consistent with the impaired DNA binding, O-GlcNAc site mutation in c-Rel greatly suppressed anti-CD3/CD28-induced gene expression of IL-2, GMCSF and IFNγ (FIG. 5C-E). However, other NF-κB-dependent genes, IκBα and A20, which has the c-Rel binding site in its promoter but is mainly induced by p65, was expressed at similar levels in both cells, indicating intact TCR signaling and NF-κB activation in these cells (FIG. 5F-G). PUGNAc treatment significantly potentiated the expression of c-Rel-dependent genes only in wild-type c-Rel expressing cells, emphasizing the role of O-GlcNAcylation in this transactivation process (FIG. 5A-E). Further confirming the PUGNAc effect, Streptozotocin (STZ), another OGA inhibitor that promotes O-GlcNAcylation, also enhanced anti-CD3/CD28-induced c-Rel-dependent gene expression (FIG. 6H). The mutant c-Rel expression did not exhibit any dominant negative effect because it did not affect the basal expression level of several c-Rel-dependent genes (FIG. 11A-D).

Example 6

Enhanced O-GlcNAcylation by PUGNAc Treatment or S350A Mutation in c-Rel does not Alter TNF Induced Gene Expression Materials and Methods Cells were treated with TNF (100 ng/ml) for 3 hrs. Jurkat T-REx cell clones expressing wild-type and mutant c-Rel were induced with doxycycline for 22 hrs, treated with PUGNAc overnight and then treated with anti-CD3/C28 for 3 hrs. Quantitative real time PCR (qPCR) was performed at least in three independent experiments in triplicates and the relative levels of indicated genes were calculated with respect to the expression of transferrin receptor. Statistical significance was determined by two-tailed unpaired Student's t test and represented as mean±SEM.

TNF-Induced Nuclear Translocation Assays.

Jurkat cells were treated overnight with PUGNAc and then with TNF. Nuclear extracts were analyzed for c-Rel and p65 nuclear translocation. p105 was used as the loading control.

TNF-Induced c-Rel O-GlcNAcylation Assays.

Jurkat cells ($40 \times 10^6$) were cultured overnight in physiological glucose concentration (5 mM) and treated with high glucose (30 mM) or N-acetylglucosamine (4 mM) for 3 hrs. TNF was applied for the last 20 min of treatment and PUGNAc was applied together with glucose for 3 hrs. Cytoplasmic and nuclear extracts were prepared and analyzed.

Results

Figure 12:
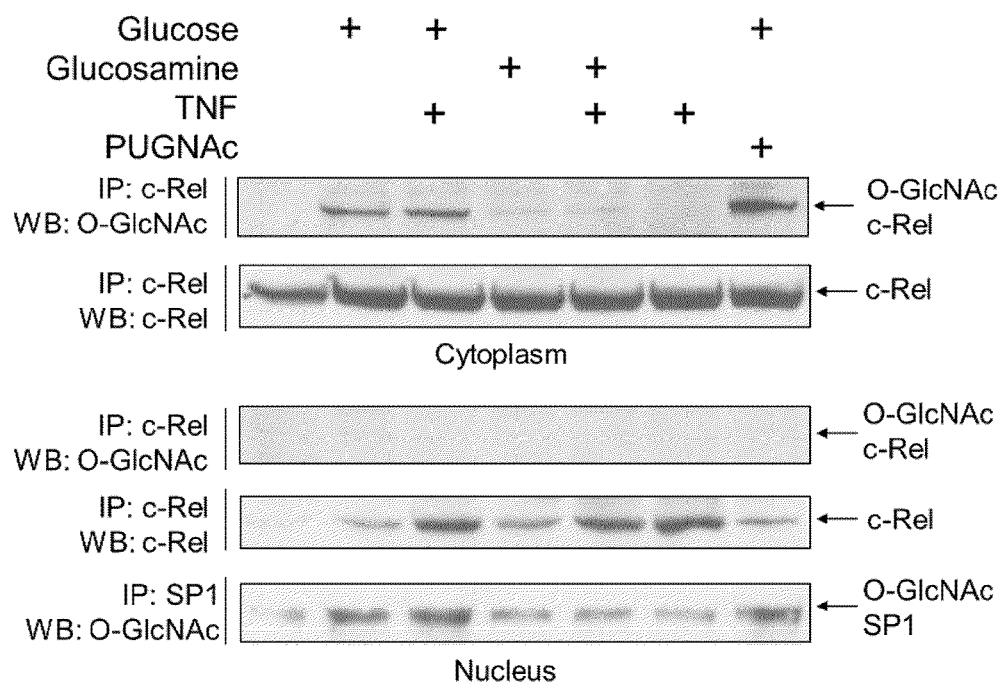
FIG. 12 shows TNF stimulation did not induce O-GlcNAcylated c-Rel in the nucleus.

TNF has been shown previously to activate c-Rel function. We studied the role of enhanced O-GlcNAcylation and c-Rel mutation in TNF-induced NF-κB-dependent gene expression. TNF-induced expression of IκBα and A20 were neither affected by the mutation in c-Rel nor by PUGNAc treatment (FIG. 6A-B). TNF did not induce the expression of IL-2 and GMCSF in these cells (FIG. 6C-D). This result either suggests that TNF induces A20 and IκBα independently of c-Rel in Jurkat T cells or they are independent of the GlcNAcylation status of c-Rel. In consistence, enhanced O-GlcNAcylation following PUGNAc treatment had no effect on TNF induced c-Rel nuclear translocation, although it decreased TNF-induced nuclear p65 levels (FIG. 6E). Further, TNF stimulation did not induce O-GlcNAcylated c-Rel in the nucleus (FIG. 6F and FIG. 12). Thus, c-Rel and its O-GlcNAcylation is stimulus specific and is important in TCR-induced, yet not in TNF-induced, expression of selected genes (Model FIG. 6G).

Our results show that O-GlcNAcylation of c-Rel is required for the transactivation of IL-2, GMCSF and IFNγ induced by TCR co-stimulation. All of these genes contain the CD28 responsive element in their promoters, suggesting a critical role of O-GlcNAcylated c-Rel in mediating CD28RE-dependent transcription. Interestingly, we did not observe any effect of c-Rel O-GlcNAc site mutation or PUGNAc treatment in TCR or TNF-induced expression of A20, and IκBα, which are previously suggested to be genetically dependent on c-Rel[47]. Increased O-GlcNAcylation did not affect TNF-induced c-Rel nuclear translocation and, conversely, TNF treatment had no significant effect on glucose or glucosamine-induced O-GlcNAcylation of c-Rel (FIG. 6F and FIG. 12). These observations suggest that TNF might induce c-Rel transactivation, independent of its O-GlcNAcylation status. TCR stimulation mediates transactivation through both O-GlcNAcylation dependent and independent pathways. Although, both TCR and TNF are capable of inducing c-Rel nuclear translocation, interestingly, only TCR activation results in O-GlcNAcylated c-Rel in the nucleus. Intuitively, this could depend on a TCR-dependent cofactor that binds O-GlcNAcylated c-Rel in the cytoplasm facilitating its nuclear translocation. Alternatively, c-Rel may get O-GlcNAcylated in the nucleus following TCR activation. These results suggest a stimulus specific role of O-GlcNAcylation in modulating c-Rel function.

OGT knockout mice and c-Rel knockout mice share common features like impaired Th1 response and OGT suppression cause impaired NF-κB activation in lymphocytes. These findings suggest an overlap in the function of O-GlcNAcylation and NF-κB. Golks et at showed that OGT is critical for NF-κB activation in lymphocytes and suggested p65 as the O-GlcNAcylated NF-κB protein. (Golks et al, *Embo J* 26:4368-4379 (2007).) Our results show that c-Rel is the major O-GlcNAcylated protein in lymphocytes and it exists in a complex with p65 (FIG. 1C-D). In addition to p65 bound c-Rel, it is also possible that c-Rel homodimer and its heterodimer with p50 are also O-GlcNAcylated, which could be tested in cells devoid of p65 or p50. Because O-GlcNAcylated c-Rel was found mostly in the cytoplasm in complex with p65, it is plausible that modified c-Rel may harness p65 in the cytoplasmic compartment and may dampen p65-dependent transcription. In support, we found that PUGNAc-mediated increase in O-GlcNAcylation decreases TNF-induced nuclear translocation of p65 (FIG. 6E). Like our results, others have also reported that PUGNAc treatment decreases p65 function in inducing some NF-κB-dependent genes. (Xing et al. *PloS one* 6:e24021 (2011).) In contrast, it has been reported that high glucose and glucosamine elevates p65 O-GlcNAcylation and enhances NF-κB-dependent transcription (James et al. *Diabetes* 51:1146-1156 (2002); Yang et al. *Proc Natl Acad Sci USA* 105:17345-17350 (2008).). These differences could arise from the cell type specificities or the type of NF-κB activating stimulus that may dictate the functional outcome of NF-κB O-GlcNAcylation.

It was shown that increases in O-GlcNAcylation of p65 decreases it affinity for IκB and facilitates p65 nuclear translocation. (Yang et al. *Proc Natl Acad Sci USA* 105: 17345-17350 (2008).) However, we did not see any marked differences in nuclear translocation of either wild-type or non-GlcNAcylatable c-Rel, lowering the possibility that O-GlcNAcylation might influence c-Rel-IκB binding. O-GlcNAcylation has been shown to facilitate DNA binding of other transcription factors like Pdx-1 (Gao et al. *Archives of biochemistry and biophysics* 415:155-163 (2003)) and YY1 (Hiromura et al. *The Journal of biological chemistry* 278: 14046-14052 (2003).). Similarly, our results suggest that O-GlcNAcylation regulates NF-κB c-Rel by facilitating its DNA binding and subsequent transactivation.

Although the present invention has been described in detail above, it will be understood by the skilled artisan that various modifications can be made without departing from the spirit of the invention. Accordingly, the invention is limited only by the following claims. All cited patents, patent applications and publications referred to in this application are herein incorporated by reference in their entirety.

What is claimed is:

1. A method of identifying a composition that can inhibit O-GlcNAcylation of c-Rel, comprising:
   providing one or more test compositions to be tested;
   testing the one or more test compositions for their ability to inhibit the attachment of N-acetylglucosamine to serine 350 of c-Rel, wherein testing comprises one or more methods selected from the group consisting of immunocytochemistry, western blot, polymerase chain reaction, mass spectrometry, immunoprecipitation, and gel shift assay; and
   identifying a test composition that inhibits the attachment of N-acetylglucosamine to serine 350 of c-Rel as an inhibitor of O-GlcNAcylation of c-Rel.

2. The method of claim 1, wherein the inhibitor is an antibody, nucleic acid, small molecule, or protein.

3. The method of claim 1, wherein testing comprises measuring the amount of O-GlcNAcylation at serine 350 in the presence of the one or more test compositions.

4. The method of claim 3, wherein the amount of O-GlcNAcylation is measured using an anti-O-GlcNAc antibody.

5. The method of claim 1, wherein testing is performed in vivo.

6. The method of claim 1, wherein testing is performed in vitro.

7. The method of claim 6, wherein testing is performed in a B lympohblastoid cell line, a T lymphoblastoid cell line, primary splenocytes or peripheral blood mononuclear cells.

8. The method of claim 1, wherein testing is performed under conditions that enhance O-GlcNAcylation.

9. The method of claim 8, wherein the conditions that enhance 0-GlcNAcylation are hyperglycemic conditions.

10. The method of claim 8, wherein the conditions of enhanced 0-GlcNAcylation are created by inhibiting O-GlcNAcase.

11. The method of claim 10, wherein O-GlcNAcase is inhibited with PUGNAc.

12. A method of identifying a composition that inhibits expression of c-Rel-dependent NF-κB-related cytokines, the method comprising:
   a) providing one or more test compositions;
   b) identifying a test composition that inhibits O-GlcNAcylation of c-Rel; and
   c) testing the test composition identified in b) for its ability to inhibit expression of c-Rel-dependent NF-κB-related cytokines in T cells, wherein testing comprises one or more methods selected from the group consisting of immunocytochemistry, western blot, polymerase chain reaction, mass spectrometry, immunoprecipitation, and gel shift assay.

13. The method of claim 12, wherein the ability to inhibit expression of c-Rel-dependent NF-κB-related cytokines is determined by measuring expression of one or more of IL-2, IFNγ and GMCSF.

14. The method of claim 12, wherein the test composition is an antibody, nucleic acid, small molecule, or protein.

15. The method of claim 12, wherein the identified test composition blocks O-GlcNAcylation of residue serine 350 of c-Rel.

16. The method of claim 12, wherein the identifying comprises testing for inhibition of O-GlcNAcylation of serine 350 of c-Rel.

17. The method of claim 16, wherein testing is performed in a B lympohblastoid cell line, a T lymphoblastoid cell line, primary splenocytes or peripheral blood mononuclear cells.

18. The method of claim 16, wherein testing is performed under conditions that enhance O-GlcNAcylation.

* * * * *